(12) United States Patent
Koller et al.

(10) Patent No.: US 7,425,426 B2
(45) Date of Patent: Sep. 16, 2008

(54) METHODS FOR PURIFICATION OF CELLS BASED ON PRODUCT SECRETION

(75) Inventors: Manfred R. Koller, San Diego, CA (US); Elie G. Hanania, San Diego, CA (US); Annabeth Fieck, San Diego, CA (US); Timothy M. Eisfeld, San Diego, CA (US)

(73) Assignee: Cyntellect, Inc., San Diego, CA (US)

(*) Notice: Subject to any disclaimer, the term of this patent is extended or adjusted under 35 U.S.C. 154(b) by 356 days.

(21) Appl. No.: 10/801,931

(22) Filed: Mar. 15, 2004

(65) Prior Publication Data
US 2005/0202558 A1    Sep. 15, 2005

(51) Int. Cl.
*C12Q 1/24* (2006.01)
(52) U.S. Cl. .................. 435/30; 435/173.4
(58) Field of Classification Search ............ 435/30, 435/173.4
See application file for complete search history.

(56) References Cited

U.S. PATENT DOCUMENTS

| | | | |
|---|---|---|---|
| 3,674,926 A | 7/1972 | Dewey et al. |
| 4,000,417 A | 12/1976 | Adkisson et al. |
| 4,165,149 A | 8/1979 | Suzki et al. |
| 4,284,897 A | 8/1981 | Sawamura et al. |
| 4,395,397 A | 7/1983 | Shapiro |
| 4,532,402 A | 7/1985 | Overbeck |
| 4,624,915 A | 11/1986 | Schindler et al. |
| 4,629,687 A | 12/1986 | Schindler et al. |
| 4,803,992 A | 2/1989 | Lemelson |
| 4,950,592 A | 8/1990 | Daiss |
| 4,998,284 A | 3/1991 | Bacus et al. |
| 5,013,660 A | 5/1991 | Kasuya et al. |
| 5,031,099 A | 7/1991 | Kettler |
| 5,035,693 A | 7/1991 | Kratzer et al. |
| 5,053,693 A | 10/1991 | Bohnert et al. |
| 5,089,384 A | 2/1992 | Hale |
| 5,093,866 A | 3/1992 | Douglas-Hamilton et al. |
| 5,103,660 A | 4/1992 | Johnson |
| 5,109,276 A | 4/1992 | Nudelman et al. |
| 5,158,889 A | 10/1992 | Hirako et al. |
| 5,188,633 A | 2/1993 | Kratzer et al. |
| 5,202,230 A | 4/1993 | Kamentsky |
| 5,235,522 A | 8/1993 | Bacus |
| 5,257,182 A | 10/1993 | Luck et al. |
| 5,272,081 A | 12/1993 | Weinreb et al. |
| 5,287,272 A | 2/1994 | Rutenberg et al. |
| 5,296,963 A | 3/1994 | Murakami et al. |
| 5,298,963 A | 3/1994 | Moriya et al. |
| 5,381,224 A | 1/1995 | Dixon et al. |
| 5,422,720 A | 6/1995 | Berndt |
| 5,428,690 A | 6/1995 | Bacus et al. |
| 5,432,865 A | 7/1995 | Kasdan et al. |
| 5,523,543 A | 6/1996 | Hunter, Jr. et al. |
| 5,590,168 A | 12/1996 | Iketaki |
| 5,646,411 A | 7/1997 | Kain et al. |
| 5,672,880 A | 9/1997 | Kain |
| 5,690,846 A | 11/1997 | Okada et al. |
| 5,719,391 A | 2/1998 | Kain |
| 5,732,150 A | 3/1998 | Zhou et al. |
| 5,784,162 A | 7/1998 | Cabib et al. |
| 5,785,703 A | 7/1998 | Goodman et al. |
| 5,790,710 A | 8/1998 | Price et al. |
| 5,795,755 A | 8/1998 | Lemelson |
| 5,828,776 A | 10/1998 | Lee et al. |
| 5,874,266 A | 2/1999 | Palsson |
| 5,890,846 A | 4/1999 | Clark et al. |
| 5,932,872 A | 8/1999 | Price |
| 5,952,651 A | 9/1999 | Morito et al. |
| 5,995,143 A | 11/1999 | Price et al. |
| 6,005,256 A | 12/1999 | McGlynn et al. |
| 6,007,814 A | 12/1999 | Scheinberg |

(Continued)

FOREIGN PATENT DOCUMENTS

EP    0 662 512    7/1995

(Continued)

OTHER PUBLICATIONS

Bird et al., "4-Hydroperoxycyclophosphamide Purged Autologous Bone Marrow Transplantation in Non-Hodgkin's Lymphoma Patients at High Risk of Bone Marrow Involvement," *Bone Marr. Transplan.*, 18:309-313 (1996).

(Continued)

*Primary Examiner*—Ralph Gitomer
(74) *Attorney, Agent, or Firm*—Knobbe, Martens, Olson & Bear LLP

(57) ABSTRACT

The invention provides methods for purifying one or more cells based on the level of one or more products secreted by the cells. In one embodiment, the method involves (a) contacting a plurality of cells immobilized in proximity to a capture matrix, the capture matrix capable of localizing a product secreted by one or more of the cells, with an agent that selectively binds to the product, the agent capable of generating a signal detectable as a property of light; (b) illuminating a population of the cells, the population contained in a frame; (c) detecting two or more properties of light directed from the frame, wherein a first property of light identifies substantially all cells of the population, and the second property of light identifies product localized to the capture matrix; (d) locating (i) substantially all cells of the population with reference to the detected first property of light, and (ii) one or more selected cells with reference to the detected second property of light, and (e) irradiating the non-selected cells, wherein each non-selected cell receives a substantially lethal dose of radiation, whereby one or more selected cells having a desired product secretion profile are purified.

90 Claims, 4 Drawing Sheets
(1 of 4 Drawing Sheet(s) Filed in Color)

U.S. PATENT DOCUMENTS

| | | | |
|---|---|---|---|
| 6,040,139 | A | 3/2000 | Bova |
| 6,099,522 | A | 8/2000 | Knopp et al. |
| 6,122,396 | A | 9/2000 | King et al. |
| 6,143,535 | A | 11/2000 | Palsson |
| 6,148,096 | A | 11/2000 | Pressman et al. |
| 6,166,385 | A | 12/2000 | Webb et al. |
| 6,215,892 | B1 | 4/2001 | Douglass et al. |
| 6,218,132 | B1 * | 4/2001 | Spack et al. ............... 435/7.24 |
| 6,275,777 | B1 | 8/2001 | Shimizu |
| 6,298,264 | B1 | 10/2001 | Zhong et al. |
| 6,315,772 | B1 | 11/2001 | Marchitto et al. |
| 6,381,224 | B1 | 4/2002 | Lane et al. |
| 6,424,863 | B1 | 7/2002 | Flock |
| 6,509,166 | B1 | 1/2003 | Edberg |
| 6,514,722 | B2 | 2/2003 | Palsson et al. |
| 6,534,308 | B1 * | 3/2003 | Palsson et al. ........... 435/288.7 |
| 6,642,018 | B1 * | 11/2003 | Koller et al. ............... 435/40.5 |
| 6,753,161 | B2 | 6/2004 | Koller et al. |
| 6,804,385 | B2 * | 10/2004 | Eisfeld et al. ............... 382/128 |
| 7,092,557 | B2 * | 8/2006 | Eisfeld et al. ............... 382/128 |
| 7,129,070 | B2 | 10/2006 | Palsson |
| 7,132,289 | B2 | 11/2006 | Kobayashi et al. |
| 2003/0219892 | A1 | 11/2003 | Palsson et al. |
| 2004/0180437 | A1 | 9/2004 | Koller et al. |
| 2005/0095578 | A1 | 5/2005 | Koller et al. |
| 2005/0118652 | A1 | 6/2005 | Lee et al. |

FOREIGN PATENT DOCUMENTS

| | | |
|---|---|---|
| JP | 63-259465 | 4/1987 |
| RU | 2054486 C1 | 2/1996 |
| WO | WO 89/01630 | 2/1989 |
| WO | WO 97/11156 | 3/1997 |
| WO | WO 98/42356 | 10/1998 |
| WO | WO 98/52016 | 11/1998 |
| WO | WO 01/40454 | 6/2001 |

OTHER PUBLICATIONS

Clarke et al., "A Recombinant Bcl-$X_s$ Adenovirus Selectively Induces Apoptosis in Cancer Cells but Not in Normal Bone Marrow Cells," *Proc. Natl. Acad. Sci.*, 92:11024-11028 (1995).

Denk, "Two-Photon Scanning Photochemical Microscopy: Mapping Ligand-Gated Ion Channel Distributions," *Proc. Natl. Acad. Sci.*, 91:6629-6633 (1994).

Dooley et al., "A Novel, Inexpensive Technique for the Removal of Breast Cancer Cells from Mobilized Peripheral Blood Stem Cell Products," *Blood*, 88:252a, Abstract 995 (1996).

Gazitt et al., "Purified CD34+Lin-Thy+ Stem Cells Do Not Contain Clonal Myeloma Cells," *Blood*, 86(1):381-389 (1995).

Grate et al., "Laser-Mediated, Site-Specific Inactivation of RNA Transcripts," *Proc. Natl. Acad. Sci.*, 96:6131-6136 (1999).

Gribben et al., "Immunologic Purging of Marrow Assessed by PCR Before Autologous Bone Marrow Transplantation for B-Cell Lymphoma," *New Engl. J. Med.*, 325(22):1525-1533 (1991).

Gulliya et al., "Elimination of Clonogenic Tumor Cells from HL-60, Daudi, and U-937 Cell Lines by Laser Photoradiation Therapy: Implications for Autologous Bone Marrow Purging," *Blood*, 73(4):1059-1065 (1989).

Guo et al., "Laser-mediated Gene Transfer in Rice," *Physiol. Plantar.*, 93:19-24 (1995).

Hanania et al., "A Novel Automated Method of Scanning Cytometry and Laser-Induced Necrosis Applied to Tumor Cell Purging," *Blood*, W.B. Sanders Company, Orlando, FL., vol. 94, No. 10, Dec. 1999, pp. 638A-639A.

Jay, "Selective Destruction of Protein Function by Chromophore-Assisted Laser Inactivation," *Proc. Natl. Acad. Sci.*, 85:5454-5458 (1988).

Krasieva et al., "Mechanisms of Cell Permeabilization by Laser Microirradiation," LAMMP, Beckman Laser Institute, University of California at Irvine, Irvine, California, 8 pp., SPIE Proceedings (1999).

Mapara et al., "Monitoring of Tumor Cell Purging After Highly Efficient Immunomagnetic Selection of CD34 Cells from Leukapheresis Products in Breast Cancer Patients: Comparison of Immunocytochemical Tumor Cell Staining and Reverse Transcriptase—Polymerase Chain Reaction," *Blood*, 89(1):337-344 (1997).

Mapara et al., "Combined Positive/Negative Purging and Transplantation of Peripheral Blood Progenitor Cell Autografts in Breast Cancer Patients: A Pilot Study," *Exper. Hemat.*, 27:169-175 (1999).

Oleinick et al., "The Photobiology of Photodynamic Therapy: Cellular Targets and Mechanisms," *Rad. Res.*, 150:S146-S156 (1998).

Palumbo et al., "Targeted Gene Transfer in Eucaryotic Cells by Dye-Assisted Laser Optoporation," *J. Photochem. Photobiol. B:Biol.*, 36:41-46 (1996).

Paulus et al., "Combined Positive/Negative Selection for Highly Effective Purging of PBPC Grafts: Towards Clinical Application in Patients with B-CLL," *Bone Marr. Transplan.*, 20:415-420 (1997).

Robertson et al., "Human Bone Marow Depleted of CD33-Positive Cells Mediates Delayed but Durable Reconstitution of Hematopoiesis: Clinical Trial of MY9 Monoclonal Antibody-Purged Autografts for the Treatment of Acute Myeloid Leukemia," *Blood*, 79(9):2229-2236 (1992).

Soughayer et al., "Characterization of Cellular Optoporation with Distance," *Anal. Chem.*, 72:1342-1347 (2000).

Theriot et al., "Comparison of Actin and Cell Surface Dynamics in Motile Fibroblasts," *J. Cell Biol.*, 119(2):367-377. (1992).

Tricot et al., CD34+THY+LIN- Peripheral Blood Stem Cells (PBSC) Effect Timely Trilineage Engraftment in Multiple Myeloma (MM), *Blood*, 86:293a, Abstract 1160 (1995).

Wagner et al., "Isolation of Small, Primitive Human Hematopoietic Stem Cells: Distribution of Cell Surface Cytokine Receptors and Growth in SCID-Hu Mice," *Blood*, 86(2):512-523 (1995).

Andersen et al., "Failure of Immunologic purging in mantle cell lymphoma assessed by polymerase chain reaction detection in minimal residual disease," Blood, 90: 4212-4221 (1997).

Borth et al., "Efficient Selection of High-Producing Subclones During Gene Amplification of Recombinant Chinese Hamster Ovary Cells by Flow Cytometry and Cell Sorting," *Institute for Applied Microbiology* pp. 266-273 (2001).

Brezinsky et al. "A Simple Method for Enriching Populations of Transfected CHO Cells for Cells of Higher Specific Productivity", *Journal of Immunological Methods* 277 (2003) 141-155.

Brittberg et al., "Treatment of deep cartilage defects in the knee with autologous chondrocyte transplantation," N.E.J.Med., 331: 889-895 (1994).

Brockstein et al., "Tumor cell contamination of bone marrow harvest products: Clinical consequences in a cohort of advanced-stage breast cancer patients undergoing high-dose chemotherapy," J. Hematotherapy, 5: 617-624 (1996).

Brugger et al., "Mobilization of Tumor Cells and Hematopoietic Progenitor Cells Into Peripheral Blood of Patients with Solid Tumors," Blood, 83: 636-640 (1994).

Campana et al., "Detection of Minimal Residual Disease in Acute Leukemia: Methodological Advances and Clinical Significance," Blood, 85: 1416-1434 (1995).

Cherlet et al., Surface IgG Content of Murine Hybridomas: Direct Evidence for Variation of Antibody Secretion Rates During the Cell Cycle *Biotechnology and Bioengineering*, vol. 47, pp. 535-540 (1995).

Chute et al., "Analysis of the steady-state dynamics organelle motion in cultured neurities," *Clin Exp Pharmco Physiol*, 22: 360 (1995).

Cossman et al., "Reed-Sternberg cell genome expression supports a B-cell lineage," *Blood*, 94: 411-416 (1999).

Deisseroth et al., "Genetic marking shows that Ph+ cells present in autologous transplants of chronic myelogenous leukemia (CML) contribute to relapse after autologous bone marrow in CML," *Blood*,83: 3068-3076 (1994).

Elbashir et al. "Duplexes of 21-nucleotide RNAs mediate RNA interference in cultured mammalian cells," Nature, 411: 494-498 (2001).

Fields et al., "Clinical significance of bone marrow-metastases as detected using the polymerase chain reaction in patients with breast cancer undergoing high-dose chemotherapy and autologous bone marrow transplantation," *J. Clin. Oncol.*, 14: 1868-1876 (1996).

Gee, Adrian P., "Part 5: Autologous Bone Marrow Purging," *Bone Marrow Processing and Purging*, 248-328 (1991).

Gray et al. "Secretion capture and report web: use of affinity derivatized agarose microdroplets for the selection of hybridoma cells" *Journal of Immunological Methods* 182 (1995) 155-163.

Greer et al., "A Clonogenic Culture Method for the Identification of Breast Cancer Cells in Marrow Aspirates of Patients Receiving High-Dose Chemotherapy," Blood, 88: 252a, Abstract 996, 439-II (1996).

Gribben et al., "Immunologic purging of marrow assessed by PCR before autologous bone marrow transplantation for B-cell lymphoma," *N.E.J. Med.*, 325: 1525-1533 (1991).

Gulati et al., "Rationale for Purging in Autologous Stem Cell Transplantation," *Journal of Hematotherapy*, 2: 467-471 (1993).

Han et al. "Quantum-dot-tagged microbeads for multiplexed optical coding of biomolecules." Nat.Biotech., 19: 631-635 (2001).

Hanania et al. "Automated In Situ Measurement of Cell-Specific Antibody Secretion and Laser-Mediated Purification for Rapid Cloning of Highly-Secreting Producers" *Wiley InterScience* (2005) 872-876.

Huang et al., "Symmetry of initial cell divisions among primitive hematopoietic progenitors is independent of ontogenic age and regulatory molecules," *Blood*, 94: 2595-2604 (1999).

Jasuja et al., "Chemotactic responses of *Escherichia coli* to small jumps of photoreleased L-aspartate," *Biophysical Journal*, 76: 1706-1719 (1999).

Koller et al., "Tissue Culture Surface Characteristics Influence the Expansion of Human Bone Marrow Cells," *Biomaterials*, 19: 1963-1972 (1998).

Kurata et al. "The laser method for efficient introduction of foreign DNA into cultured cells." Exp.Cell Res., 162: 372-378 (1986).

Langer et al., "The challenges ahead," *Sci. Am.*, 280: 86-89 (1999).

Lazarus et al., "Does In Vitro Bone Marrow Purging Improve the Outcome after Autologous Bone Marrow Transplantation?," *Journal of Hematotherapy*, 2: 457-466 (1993).

Lydaki et al., "Merocyanine 540 mediated photolysis of normal bone marrow, committed hemopoietic progenitors and neoplastic cells. Implications for bone marrow purging," *Leukemia Research*, 21: 641-650, no date given.

Lydaki et al., "Merocyanine 540 mediated photoirradiation of leukemic cells. In vitro inference on cell survival," *Journal of Photochemistry and Photobiology B: Biology*, 32: 27-32 (1996).

Meilhoc et al., "Application of Flow Cytometric Measurement of Surface IgG in Kinetic Analysis of Monoclonal Antibody Synthesis and Secretion by Murine Hybridoma Cells", *Journal of Immunological Methods*, 121 (1989) 167-174.

Miller et al., "Rapid Killing of Single Neurons by Irradiation of Intracellular Injected Dye," *Science*, 206: 702-704 (1979).

Niemz, M. H., "Laser-tissue interactions: Fundamentals and applications," Springer-Verlag, (1996).

Nilius et al. "A novel type of cardiac calcium channel in ventricular cells," Nature, 316: 443-6 (1985).

Oh et al., "Phototoxicity of the Fluorescent Membrane Dyes PKH2 and PKH26 on the Human Hematopoietic KG1a Progenitor Cell Line," *Cytometry*, 36: 312-318 (1999).

Pedersen, R. A., "Embryonic stem cells for medicine," *Sci. Amer.*, 280: 68-73 (1999).

Photonic Instruments, Inc.; Micro Point-Laser System for Bio-Medical and Life Sciences; Product Information Sheet, Apr. 1996.

Rill et al., "Direct Demonstration that Autologous Bone Marrow Transplantation for Solid Tumors Can Return a Multiplicity of Tumorigenic Cells," *Blood*, ; 84: 380-383 (1994).

Rowley, Scott D., "Pharmacological Purging of Malignant Cells; Bone Marrow Transplantation," *Boston-Blackwell Scientific Publications*, 164-178 (1994).

Sagi et al. "Gene delivery into prostate cancer cells by holmium laser application." Prostate Cancer and Prostatic Diseases, 6: 127-130 (2003).

Schulze et al., "Tumor cell contamination of peripheral blood stem cell transplants and bone marrow in high-rsik breast cancer patients," *Bone Marrow Transplant.*, 19: 1223-1228 (1997).

Schutze et al., "Identification of expressed genes by laser-mediated manipulation of single cells," *Nature Biotechnol.*, 16: 737-742 (1998).

Sharp et al., Significance of detection of occult Non-Hodgkin's Lymphoma in histologically uninvolved bone marrow by a culture technique, *Blood*, 79: 1074-1080 (1992).

Sharp et al., "Outcome of high-dose therapy and autologous transplantation in non-Hodgkin's lymphoma based on the presence of tumor in the marrow or infused hematopoietic harvest," *J. Clin. Oncol.*, 14: 214-219 (1996).

Shirahata et al. "New technique for gene transfection using laser irradiation." J.Invest.Med., 49: 189-190 (2001).

Tao et al. "Direct gene transfer into human cultured cells facilitated by laser micropuncture of the cell membrane." PNAS, 84: 4180-4184 (1987).

Theocharous et al., "The Detection and Genetic Analysis of Low Frequency Epithelial Tumor Cells in Patients with Breast Cancer," Blood, 88: 252a, Abstract 998, 441-II (1996).

Thomas et al., "Direct Purging of Breast Carcinoma Cells with Anti-CD24 and/or Anti-Breast Carcinoma Antibodies Using a Novel Immunomagnetic Cell Depletion System," *Blood*, 88: 252a, Abstract 997, 440-II (1996).

Tirlapur et al. "Targeted transfection by femtosecond laser." Nature, 418: 290-291 (2002).

Tsukakoshi et al. "A novel method of DNA transfection by laser microbeam cell surgery." Appl. Phys. B. 35: 135-140 (1984).

Vannucchi et al., "Evaluation of breast Tumor cell contamination in the bone marrow and leukapheresis collections by RT-PCR for cytokeratin-19 mRNA," *Br. J. Haematol.*, 103: 610-617 (1998).

Vervoordeldonk et al., PCR-positivity in harvested bone marrow predicts relapse after transplantation with autologous purged bone marrow in children in second remission of precursor B-cell acute leukemia, *Br. J. Haematol.*, 96: 395-402 (1997).

Vredenburgh et al., "The significance of tumor contamination in the bone marrow from high-risk primary breast cancer patients treated with high-dose chemotherapy and hematopoietics support," *Biol. Blood Marrow Transplant.*, 3: 91-97 (1997).

International Search Report from PCT/US01/07506, 2001.

International Search Report from PCT/US00/32742, 2001.

Atochina et al., "Comparison of results using the gel microdrop cytokine secretion assay with Elispot and intracellular cytokine staining assay," Cytokine 27 (2004) 120-128.

Holmes et al., "Improved cell line development by a high throughput affinity capture surface display technique to select for high secretors," Journal of Immunological Methods 230 (1999) 141-147.

Manz et al., "Analysis and sorting of live cells according to secreted molecules, relocated to a cell-surface affinity matrix," Proc. Natl. Acad. Sci. vol. 92, pp. 1921-1925 (Mar. 1995).

Miller, Diane MSc., Monoclonal Antibody Production, Stem Cell Technologies (www.stemcell.com), Mini-Review pp. 1-2 No Date Given.

Pearson et al., "Methods for Derivation and Detection of Anti-Parasite Monoclonal Antibodies," Journal of Immunological Methods, 34 (1980) 141-154.

Powell et al., "Gel Microdroplets and Flow Cytometry: Rapid Determination of Antibody Secretion by Individual Cells Within A Cell Population," Nature Publishing Group, Bio/Technology vol. 9 (Apr. 1990).

* cited by examiner

METHODS FOR PURIFICATION OF CELLS BASED ON PRODUCT SECRETION

BACKGROUND OF THE INVENTION

This invention relates generally to cell purification and, more specifically to methods for purifying cells based on the level of one or more products secreted by the cells.

The ability to obtain a purified cell line is fundamental in a growing number of basic research and applied commercial applications. For example, in drug discovery, use of a homogeneous population of cells that express a particular drug target allows for reproducible results, and therefore permits high-throughput screening. For this reason, a cell clone that stably expresses a drug target can be a prerequisite for initiating a drug screening campaign that can span several months and hundreds of thousands of candidate drugs.

Drug discovery efforts also depend on measuring cell responses, many of which can be in the form of secreting various cellular products that do not stay associated with the cell that produced them. For example, immune system cells can secrete numerous cytokines (interferons, interleukins and the like) that impact disease processes. The ability to easily purify cells based on their secretion response profile is therefore important. The absence of secretion of a particular product can be equally important in this setting.

In biopharmaceutical manufacturing, over $30 billion worth of products are produced annually, many from large-scale cultures of cloned cell lines producing a secreted protein. These products include monoclonal antibodies (for example, Herceptin® (anti-EGFR), Rituxan® (anti-CD20), Xolair® (anti-IgE)), cytokines (for example, Aranesp® (erythropoietin), Rebif® (interferon)), and numerous other proteins (for example, Factor VIII, TPA, FSH, BMP). Generation of cell lines for manufacturing these products is subject to many stringent requirements, including high protein secretion, low biomass production, adaptation to defined serum-free medium, and adaptation to bioreactor conditions. Isolation of a purified cell to generate a cell line can therefore be a critical aspect of preparing cell-based products. In the manufacturing setting, validation of cell cloning for product-producing cell lines is an added requirement. For example, one requirement of the United States Food and Drug Administration (FDA) is verification of the origin of each cell clone developed for manufacturing.

Currently, a variety of methods are used for purifying cells, such as to obtain a single cell for generating a clonal cell line. One technique involves seeding cells at low density, identifying cells/colonies with desirable attributes and isolating or collecting them by use of cloning rings or micropipette transfer. This approach provides visual verification of clonality at the time the cells/colonies are isolated. The considerable drawback is the slow and laborious procedure required to isolate and transfer each cell/colony into a new culture for evaluation. Further, this technique can be difficult to impossible to implement with cells that exhibit a low cloning efficiency, such as primary cells.

Another commonly used technique for purifying cells involves seeding cells at limiting dilution in multi-well plates (that is, maximizing the probability that many wells will receive only one cell). Under the best circumstances (for example, no cell clumping), one can expect ~37% of wells to initially receive one cell. However, not all wells will result in cell growth, and wells receiving more than one cell usually have a growth advantage due to medium conditioning effects. Consequently, many of the "clones" generated from limiting dilution are not clonal, and three to five serial sub-cloning steps are required to improve the likelihood of achieving a clonal population. The success of limiting dilution can be improved by visual identification of wells receiving single cells, but this process is slow and laborious. Further, limiting dilution is difficult to implement with cells that have low cloning efficiency, such as primary cells. Finally, before a secreted product from a cell can be measured, the cell must be allowed to proliferate to obtain enough secreted product to be detected (such as by ELISA of the culture supernatant).

An additional commonly used technique for purifying cells involves flow cytometry. Flow cytometers process cells by suspending them in a fast-moving fluid stream, passing them through a laser beam/detector system to assess each cell's fluorescence and laser scattering characteristics, and then ejecting them from a nozzle within electrically-charged liquid droplets that are then deflected into a tube for collection. Although flow cytometry works well for non-adherent cell types (for example, blood cells), it is poorly suited for many other cell types (for example, neurons, hepatocytes) due to the harsh flow cytometry conditions, particularly when such cells are being sorted at one per well for cloning. Unfortunately, flow cytometry cannot be used to detect secreted cell products because the cells are suspended in a dynamic liquid stream. Although a bead-encapsulation method that allows secreted product detection by flow cytometry has been developed, this approach adds the complexities of encapsulating the cells, verifying the contents (that is, clonality) of each capsule, and then recovering the single cells of interest from the capsules.

Cell purification also is commonly accomplished by growing transfected cells in selective media. In selecting transfected mammalian cells, drug resistance is often used as a selection criterion because successfully transfected cells express both a protein of interest and a drug resistance gene product. Disadvantages of this approach include unintended physiological effects of the drug and the resistance gene product, and the current lack of acceptance by the FDA of this approach for production of biopharmaceuticals.

Thus, there exists a need for efficient methods for purifying cells based on their product-secretion profile. The invention satisfies this need and provides related advantages as well.

SUMMARY OF THE INVENTION

The invention provides methods for purifying one or more cells. In one embodiment, the method involves (a) contacting a plurality of cells immobilized in proximity to a capture matrix, the capture matrix capable of localizing a product secreted by one or more of the cells, with an agent that selectively binds to the product, the agent capable of generating a signal detectable as a property of light; (b) illuminating a population of the cells, the population contained in a frame; (c) detecting two or more properties of light directed from the frame, wherein a first property of light identifies substantially all cells of the population, and the second property of light identifies product localized to the capture matrix; (d) locating (i) substantially all cells of the population with reference to the detected first property of light, and (ii) one or more selected cells with reference to the detected second property of light, and (e) irradiating the non-selected cells, wherein each non-selected cell receives a substantially lethal dose of radiation, whereby one or more cells having a desired product secretion profile are purified.

The invention provides another method for purifying one or more cells. The method involves (a) illuminating a population of cells in a frame, wherein the illuminated cells are contained in a plurality of cells immobilized in proximity to a capture matrix, the capture matrix capable of localizing a product secreted by one or more of the cells; (b) detecting two or more properties of light directed from the frame, wherein a first property of light identifies substantially all cells of the population, and a second property of light identifies product localized to the capture matrix; (c) locating (i) substantially all cells of the population with reference to the detected first property of light, and (ii) one or more selected cells with reference to the detected second property of light, and (d) irradiating the non-selected cells, wherein each non-selected cell receives a substantially lethal dose of radiation, whereby one or more cells having a desired product secretion profile are purified.

The invention provides a further method for purifying one or more cells. The method involves (a) illuminating a population of cells in a frame, wherein the illuminated cells are contained in a plurality of cells immobilized in proximity to a capture matrix, the capture matrix capable of localizing a product secreted by one or more of the cells; (b) detecting at least one property of light directed from the frame, wherein a property of light identifies product localized to the capture matrix; (c) locating (i) one or more selected cells with reference to the detected property of light, and (ii) one or more domains in the frame, each domain corresponding to an area occupied by at least one selected cell, wherein the one or more domains are located with reference to the detected property of light; and (d) irradiating the non-domain area contained in the frame, wherein substantially all cells present within the non-domain area receive a substantially lethal dose of radiation, whereby one or more cells having a desired product secretion profile are purified.

An additional method for purifying one or more cells provided by the invention involves (a) contacting a plurality of cells immobilized in proximity to a capture matrix, the capture matrix capable of localizing a product secreted by one or more of the cells, with an agent that selectively binds to the product, the agent capable of generating a signal detectable as a property of light; (b) illuminating a population of the cells, the population contained in a frame; (c) detecting at least one property of light directed from the frame, wherein a property of light identifies product localized to the capture matrix; (d) locating (i) one or more selected cells with reference to the detected property of light, and (ii) one or more domains in the frame, each domain corresponding to an area occupied by at least one selected cell, wherein the one or more domains are located with reference to the detected property of light, and (e) irradiating the non-domain area contained in the frame, wherein each cell present within the non-domain area receives a substantially lethal dose of radiation, whereby one or more cells having a desired product secretion profile are purified.

The methods of the invention can be used, for example, to purify a cell that secretes a polypeptide. Non-limiting examples of polypeptides that can be secreted by a purified cell include an antibody, an antibody fragment, a cytokine, a growth factor, an enzyme, a hormone, a neurotransmitter, a signaling molecule, and a therapeutic protein. The capture matrix employed in a method of the invention can include, for example, Protein G, Protein A, an antibody, an antibody fragment, an aptamer, or a ligand for the product.

A method of the invention for purifying one or more cells can additionally involve illuminating a further population of the cells, the further population contained in a further frame, and repeating the detecting, locating and irradiating steps. This sequence can be repeated until substantially all of the non-selected cells in the plurality of cells receive a substantially lethal dose of radiation, if desired.

The one or more cells purified using a method of the invention can be, for example, cells that produce a desired amount of product relative to other cells of the population. Such a desired amount of product can be a high or low level of product secretion relative to other cells of the population. In addition, a method of the invention can be used to purify a cell that lacks secretion of a product.

BRIEF DESCRIPTION OF THE DRAWINGS

The patent or application file contains one drawing executed in color. Copies of this patent or patent application publication with the color drawing will be provided by the Office upon request and payment of the necessary fee.

DETAILED DESCRIPTION OF THE INVENTION

Figure 1:
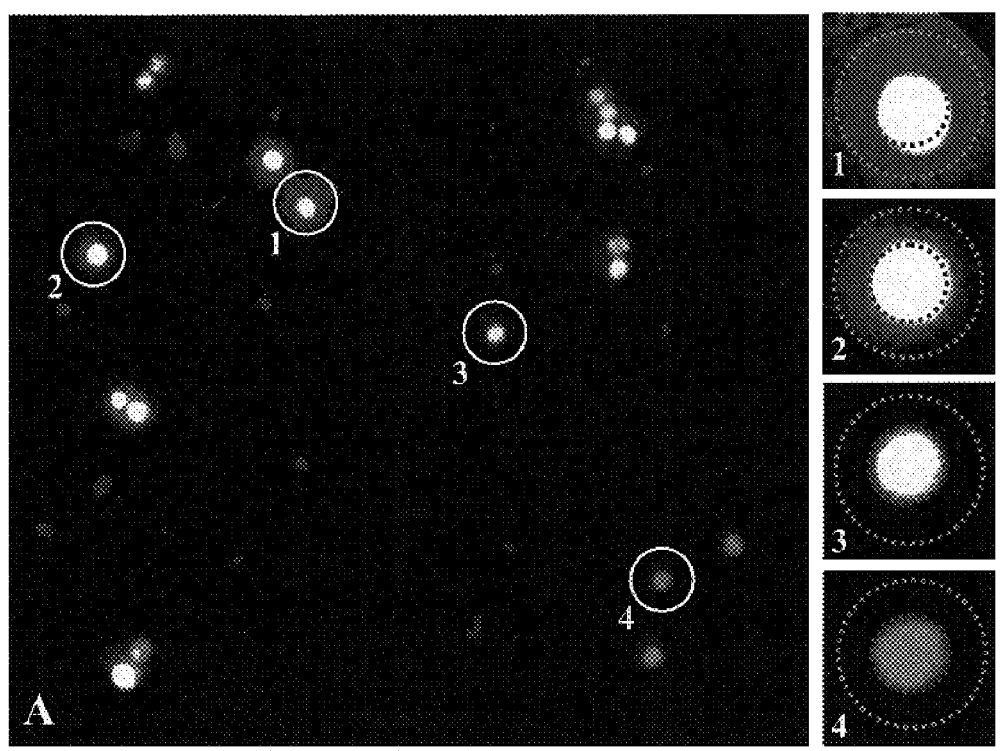
FIG. 1 shows in situ localization and detection of secreted antibody (red) in proximity to immobilized hybridoma cells (green) (A). Also shown is the selection of cells based on the level of antibody secretion from individual hybridoma cells, ranging from (1) high, (2) moderate, (3) low, and (4) undetectable.

The present invention is directed to methods for purifying cells that have a desired product secretion profile based on in situ capture and detection of the secreted product and elimination of unwanted cells via treatment with a substantially lethal dose of radiation. The methods of the invention can be used, for example, to purify one or more cells that secrete a product at a high level, intermediate level or low level, or to purify one or more cells that lack detectable secretion of the product.

In one embodiment, the method for purifying one or more cells involves selecting cells from among the cells of a population in which some members are expected to secrete one or more particular products, and targeting the remaining cells individually for elimination by a substantially lethal dose of radiation. To practice the method, a capture matrix is used to localize the secreted product in the vicinity of each secreting cell of an immobilized population of cells. As such, each cell in proximity to the capture matrix can be characterized by the presence of surrounding captured product. To determine the presence of secreted product in the vicinity of a cell, an agent that selectively binds to the product is contacted with the capture matrix, and a signal generated by the agent is detected. The signal generated is a property of light that corresponds to the secreted product. Another property of light is used to identify substantially all cells of the population.

Because the cells are immobilized and product secreted by a cell is retained in the vicinity of the secreting cell by the capture matrix, the property of light corresponding to the secreted product is generally apparent as a circle or halo surrounding the secreting cell. Product-secreting cells are then selected, depending upon the desired amount of product secretion; alternatively, cells can be selected that lack a detectable amount of product secretion. Once desired cells are selected, non-selected cells of the population are irradiated with a substantially lethal dose of radiation. By eliminating the unwanted cells, one or more desired cells are purified. This procedure is performed on a population of cells contained in a frame, which is the portion of the sample captured in an image. This procedure can be repeated for additional populations of cells contained in further frames, for example, until every frame has been processed and all unwanted cells have been treated with a substantially lethal dose of radiation. The remaining one or more cells represent selected cells having a desired product secretion profile. Furthermore, such remaining selected cells can be allowed to proliferate, if desired.

In another embodiment, the method for purifying one or more cells involves purifying the desired cells without specific knowledge of the location of unwanted cells. In this method, the selected cells are located with reference to a detected property of light corresponding to the captured product, and one or more domains corresponding to areas occupied by at least one selected cell are determined. Unwanted cells, which are present in the non-domain area, are treated with a substantially lethal dose of radiation and are thereby eliminated.

Using the methods of the invention, cells can be purified based on the level or rate of secretion of a product. For example, when it is desired to obtain one or more cells that have a high level or rate of secretion of the product relative to other cells of the population, cells other than the selected high secretors can be eliminated. Alternatively, the methods of the invention can be used, for example, to obtain one or more cells that have an intermediate level or rate of secretion of the product relative to other cells of the population; to obtain one or more cells that have a low level or rate of secretion of the product relative to other cells of the population, and to obtain one or more cells that have a minimal or undetectable level or rate of secretion of the product relative to other cells of the population. Moreover, cells can be purified based on the level or rate of secretion of more than one product secreted by the cell, as well as based on a ratio of the level or rate of secretion of two or more products secreted by the cell.

The number of cells purified from a particular sample being treated using a method of the invention will depend upon application of the method. For example, if a clonal population of cells is desired, the methods of the invention can be used to eliminate all but one selected cell. The selected cell can then be allowed to proliferate to obtain a clonal population. Alternatively, the methods can be used to purify two or more cells.

The methods of the invention can be used, for example, to purify one or more cells that have a low cloning efficiency, such as primary cells. As an example, a desired cell can be selected, and then all but 10, 20, 50, or more other cells can be eliminated. The temporarily spared cells can be located near or far from the desired cell to serve as helper cells that provide medium conditioning for the desired cell. As the desired cell grows and creates a clonal population that can be sustained on its own, the helper cells and their progeny can be eliminated from the well at a later time.

As used herein, the term "product" means a substance produced by a cell and released from its plasma membrane such that the product can exist apart from the cell and therefore can be localized to a capture matrix. A product secreted by a cell used in a method of the invention can include, for example, a non-polypeptide compound or a polypeptide. Non-limiting examples of a non-polypeptide compound include an ion and organic molecule, such as a hormone, signaling molecule, or neurotransmitter. Non-limiting examples of a polypeptide include an antibody or fragment thereof; a polypeptide that functions as a signaling molecule, such as a cytokine, growth factor, hormone or neurotransmitter, and an enzyme. Therefore, the methods of the invention can be used to purify a cell that secretes one or more of a variety of useful polypeptides, such as a therapeutic protein. As used herein, the term "antibody" includes both polyclonal and monoclonal antibodies, as well as antigen binding fragments of such antibodies (for example, Fab, F(ab')2, Fd and Fv fragments and the like). In addition, the term "antibody" is intended to encompass non-naturally occurring antibodies, including, for example, single chain antibodies, chimeric antibodies, bifunctional antibodies, CDR-grafted antibodies and humanized antibodies, as well as antigen-binding fragments thereof.

A product secreted by a cell used in a method of the invention can impart a property of light or can be bound by an agent that imparts a property of light. A product that imparts a property of light can be naturally-occurring, such as a naturally-occurring luminescent or fluorescent molecule, or can be genetically engineered, such as a recombinantly expressed luminescent or fluorescent protein (for example, green fluorescent protein (GFP) or a GFP variant, or a fusion protein containing a luminescent or fluorescent moiety).

As used herein, the term "product secretion profile" means the level or amount of one or more products secreted by a cell. The amount of a product secreted by a cell is generally assessed relative to other cells of the population in the frame, or relative to other cells of the plurality. The amount of a product secreted by a cell can be determined qualitatively or quantitatively, depending on the sensitivity desired for a particular application of the method. A product secretion profile can refer to the amount of secretion of one product or more than one product, such as two or more products, three or more products and four or more products. An exemplary expression of a product secretion profile for more than one product is a ratio representing the amounts of two or more different products. As is described herein below, the amount of a product secreted by a cell can include an undetectable level of product.

The "cells" used in a method of the invention can be any biological cells, including prokaryotic and eukaryotic cells, which can be naturally-occurring or genetically engineered cells. Exemplary cell types include animal cells, such as cells from human, non-human primates, rats and mice; plant cells; yeast cells; insect cells, and bacteria cells. Naturally-occurring cells can be obtained from an organism, and if desired, can be adapted to tissue culture prior to use in the methods of the invention. Genetically engineered cells can be prepared using routine laboratory methods, described, for example, in standard molecular biology technical manuals, such as Sambrook et al., *Molecular Cloning: A Laboratory Manual*, Cold Spring Harbor Laboratory, New York (1992) and Ansubel et al., *Current Protocols in Molecular Biology*, John Wiley and Sons, Baltimore, Md. (1998). Examples of cells commonly used to recombinantly express proteins include cell lines such as COS, CHO, HeLa, NIH3T3, HEK 293-T and PC12; insect cells (for example, *Drosophila*); yeast cells (for example, *S. cerevisiae*, *S. pombe*, and *Pichia pastoris*) and prokaryotic cells (for example, *E. coli.*)

The methods of the invention for purifying one or more cells involve use of cells that are immobilized in proximity to a capture matrix. As used herein, the term "capture matrix" means a substance capable of sequestering or binding a secreted product in the vicinity of the secreting cell. The capture matrix can be coated, adhered, or otherwise present on a variety of surfaces, which can include slides, plates, wells, tubes, vessels, arrays, particles and other configurations of matter that provide a surface or three-dimensional space that can contain cells.

A capture matrix can localize a product secreted by a cell by selectively binding or non-selectively sequestering the product. A product can be selectively bound, for example, by interacting with a specific binding partner that "captures" the product, the specific binding partner being linked to or associated with the "matrix." A product can be sequestered non-selectively, for example, by interacting with a non-specific binding partner that is linked to or associated with the matrix, and by physical containment within the vicinity of the secreting cell by the matrix.

A capture matrix useful in the invention can include a variety of stationary substances, including, for example, gels, resins, packed beads, membranes and the like. A capture matrix can comprise a variety of materials, with non-limiting examples of such materials being optical glass, silica, agarose, agar, gelatin, methylcellulose and polymers such as polyacrylamide, polystyrene, and nylon. The stationary substance can be selected to have a pore size that allows sequestering of secreted product in the vicinity of the cell, if desired. The stationary substance also can be selected to have a reactive surface that allows linking of one or more product binding partners and/or cell binding partners. The stationary substance further can be selected to allow embedding or penetration of binding partners into the matrix.

The stationary substance optionally can be linked to a specific binding partner for the secreted product, which can be any molecule that interacts with the product but does not substantially interact with unrelated molecules, or a non-specific binding partner for the secreted product, which can be any molecule that interacts with the product. A non-limiting example of a product and corresponding specific binding partner is an antibody and antigen; a non-limiting example or a product and corresponding non-specific binding partner is an antibody and Protein A or G. Exemplary binding partners for a secreted product that can be contained in a capture matrix therefore include an antibody or antibody fragment, a product-binding nucleic acid molecule such as an aptamer, a ligand, receptor or substrate for the product, Protein A, Protein G, a mixture of Proteins A and G, and the like. The stationary substance further can be linked to a molecule that binds to a cell. The molecule that binds to the cell can bind selectively or non-selectively. Non-limiting examples of molecules useful for binding cells include an antibody and a substrate for a cell surface receptor, such as polylysine, fibronectin, collagen and the like.

As used herein the phrase "immobilized in proximity to" when used in reference to the location of cells with respect to the capture matrix, means that the cells are located on, within or are closely associated with the capture matrix such that a detectable amount of product secreted by the immobilized cell remains in the vicinity of the cell. A cell can be immobilized in proximity to a capture matrix, for example, by adhering to the capture matrix in a non-specific manner and by binding to one or more components of the capture matrix in a specific manner. If desired, a cell can be genetically engineered to express a molecule that binds to a component of the capture matrix, or can be labeled with such a molecule. For example, a biotinylated cell will bind with high affinity to an avidin molecule contained in or on the capture matrix.

The methods of the invention can employ an agent that selectively binds to a secreted product. As used herein, the term "selective" when used in reference to an agent that binds to a secreted product means that the agent binds to the product without substantially cross-reacting with other molecules. The affinity of an agent that selectively binds to a secreted product will generally be greater than about $10^{-5}$ M and more preferably greater than about $10^{-6}$ M. High affinity interactions can be preferred, and will generally be greater than about $10^{-8}$ M to $10^{-9}$ M. Examples of agents that can selectively bind to a secreted product include an antibody or fragment thereof, a small organic compound, peptide, a nucleic acid molecule or protein-nucleic acid molecule or a derivative thereof that has been determined to bind the secreted product without substantial cross reactivity with unrelated molecules. Non-limiting specific examples of agents that bind selectively to a secreted product include a polyclonal antibody selective for the product, a monoclonal antibody selective for the product, a protein-nucleic acid molecule selective for the product, an oligonucleotide, such as an aptamer, selective for the product; a substrate for the product and a ligand of the product.

In the methods of the invention, an agent that selectively binds to the product is capable of generating a signal detectable as a property of light. Such a signal can be, for example, light of a particular wavelength, fluorescence lifetime, fluorescence polarization, fluorescence absorption, fluorescence emission, or FRET of a moiety integral to the agent, attached covalently or non-covalently to the agent, or contained within or on the agent. Exemplary fluorescent and chromogenic moieties include AlexaFluor Dyes, BODIPY fluorophores, fluorescein, Oregon Green, eosins and erythrosins, Rhodamine Green, tetramethylrhodamine, Lissamine Rhodamine B and Rhodamine Red-X Dyes, Cascade Blue dye, coumarin derivatives, and naphthalenes, including dansyl chloride.

In one embodiment, a property of light is used to identify substantially all cells of the population. As used herein in reference to identifying cells, the term "substantially all cells" means every cell of the population detected within the limits of the optical system employed. Therefore, it is understood that cells at particular locations, such as on the margin of the frame or field-of-view, or cells having a shape uncharacteristic of the cell type being used, such as cells that are uncharacteristically flat or small, can be undetectable.

A property of light associated with substantially all cells of a population can be imparted by the cells themselves, such as brightfield or darkfield light microscopy transmission, by a component of the cells, or by a reagent that binds to the cells. A component of a cell that imparts a property of light can be naturally-occurring, such as a naturally-occurring luminescent or fluorescent molecule, or can be genetically engineered, such as a recombinantly expressed luminescent or fluorescent protein (for example, green fluorescent protein (GFP) or a GFP variant). A variety of reagents that bind to cells and generate a property of light are well known in the art and include, for example, labeled antibodies; organic molecules; vesicles; monolayer and multilayer assemblies; quantum dots, and other microscopic particles having incorporated dyes that generate a property of light. Exemplary reagents that generate a property of light include CELL TRACKER blue, CELL TRACKER yellow-green, CELL TRACKER orange, CELL TRACKER green, Calcein AM (Molecular Probes, Eugene, Oreg.), PKH fluorescent linker dyes (Sigma) and Qdot nanocrystals (Quantum Dot Corporation). A property of light associated with substantially all cells of a population can correspond, for example, to the cell surface or a portion thereof, the cytoplasm or a portion thereof, or an organelle, such as the nucleus. If desired, a reagent can be used to assess the viability of cells of the population, for example, by differentiating between living and dead cells. Reagents useful for identifying nonviable cells are well known to those skilled in the art and include, for example, SYTOX Blue (Molecular Probes, Eugene, Oreg.).

The methods of the invention involve treating unwanted cells with a substantially lethal dose of radiation. As used herein, the terms "substantially lethal" when used in reference to a radiation dose means that the amount of radiation received by the cell is sufficient to damage the cell to the extent that cell death occurs. The cell death process can occur immediately upon treatment, or minutes, hours or even days after treatment; the length of the useful period of time over which death occurs will depend upon the particular needs of the application. It is understood that a particularly resilient cell can remain viable after receiving a dose of radiation effective for causing death of a particular cell type. A substantially lethal dose of radiation can cause death of at least 97% of treated cells, including 98% of treated cells, 99% of treated cells and 100% of treated cells.

An advantage of the methods of the invention for purifying one or more cells is that the one or more cells can be selected and purified based on their product secretion profile without any need to use chemical selection or to detach and transfer a selected cell to a different vessel during the purification. A general overview of a method useful for purifying a selected cell is as follows. Cells are plated on a capture matrix present on or in a sample container such as a multi-well plate, and are allowed to secrete a protein product. The protein product, if secreted, binds to or is localized by the capture matrix. Secreted product is then detected based on a property of light associated with the product or a property of light associated with an agent bound to the product. As such, the product detection process can involve contacting the secreted product with an agent that selectively binds to the product, with excess reagent being removed from the sample if required, to obtain an acceptable signal over background. The cells with the desired product secretion profile are then selected based on a signal corresponding to the property of light. Once the desired cells are selected, the remaining cells are eliminated. The elimination of unwanted cells can be performed by substantially lethal irradiation of the cells individually or en masse. A selected cell once purified is allowed to proliferate for several days. Any non-selected cells that survive radiation treatment can be removed by repeating the substantially lethal irradiation, if necessary. The colony resulting from proliferation of the selected cell is then transferred to a culture dish, and product secretion is confirmed. In this manner, a clonal population of cells with a desirable product secretion profile can be obtained.

A method of the invention can be used to purify one or more cells that lack detectable secretion of an undesirable product. A general overview of a method useful for purifying such cells is as follows. Cells are plated on a capture matrix present on or in a sample container such as a multi-well plate, and are allowed to secrete a product. All cells of the population are identified based on a first property of light associated with all cells, and secreted product is detected based on a second property of light associated with the product or an agent bound to the product. Cells lacking detectable secretion of the product are then selected by identifying a cell having an undetectable signal corresponding to secreted product. Once the desired non-secreting cells are selected, the remaining cells are eliminated. The elimination of unwanted cells can be performed by substantially lethal irradiation of the cells individually or en masse. The selected non-secreting cell once purified can be allowed to proliferate for several days. Any non-selected cells that survive the radiation treatment can be removed by repeating the substantially lethal irradiation, if necessary. The colony resulting from proliferation of the selected cell is then transferred to a culture dish, and lack of product secretion is confirmed. In this manner, a clonal population of cells that lack detectable secretion of a product can be obtained.

In one embodiment, the method for purifying one or more cells involves (a) contacting a plurality of cells immobilized in proximity to a capture matrix, the capture matrix capable of localizing a product secreted by one or more of the cells, with an agent that selectively binds to the product, the agent capable of generating a signal detectable as a property of light; (b) illuminating a population of the cells, the population contained in a frame; (c) detecting two or more properties of light directed from the frame, wherein a first property of light identifies substantially all cells of the population, and the second property of light identifies product localized to the capture matrix; (d) locating (i) substantially all cells of the population with reference to the detected first property of light, and (ii) one or more selected cells with reference to the detected second property of light, and (e) irradiating the non-selected cells, wherein each non-selected cell receives a substantially lethal dose of radiation, whereby one or more cells having a desired product secretion profile are purified. The method can further involve the step of (f) illuminating a further population of the cells, the further population contained in a further frame, and repeating steps (c) through (e).

In another embodiment, the method involves (a) illuminating a population of cells in a frame, wherein the illuminated cells are contained in a plurality of cells immobilized in proximity to a capture matrix, the capture matrix capable of localizing a product secreted by one or more of the cells; (b) detecting two or more properties of light directed from the frame, wherein a first property of light identifies substantially all cells of the population, and a second property of light identifies product localized to the capture matrix; (c) locating (i) substantially all cells of the population with reference to the detected first property of light, and (ii) one or more selected cells with reference to the detected second property of light, and (d) irradiating the non-selected cells, wherein each non-selected cell receives a substantially lethal dose of radiation, whereby one or more cells having a desired product secretion profile are purified.

The invention provides an additional method for purifying one or more cells. The method involves (a) illuminating a population of cells in a frame, wherein the illuminated cells are contained in a plurality of cells immobilized in proximity to a capture matrix, the capture matrix capable of localizing a product secreted by one or more of the cells; (b) detecting at least one property of light directed from the frame, wherein a property of light identifies product localized to the capture matrix; (c) locating (i) one or more selected cells with reference to the detected property of light, and (ii) one or more domains in the frame, each domain corresponding to an area occupied by at least one selected cell, wherein the one or more domains are located with reference to the detected property of light; (d) irradiating the non-domain area contained in the frame, wherein substantially all cells present within the non-domain area receive a substantially lethal dose of radiation, whereby one or more cells having a desired product secretion profile are purified. The method can further involve the step of (e) illuminating a further population of the cells, the further population contained in a further frame, and repeating steps (b) through (d).

An additional method for purifying one or more cells provided by the invention involves (a) contacting a plurality of cells immobilized in proximity to a capture matrix, the capture matrix capable of localizing a product secreted by one or more of the cells, with an agent that selectively binds to the product, the agent capable of generating a signal detectable as a property of light; (b) illuminating a population of the cells, the population contained in a frame; (c) detecting at least one property of light directed from the frame, wherein a property of light identifies product localized to the capture matrix; (d) locating (i) one or more selected cells with reference to the detected property of light, and (ii) one or more domains in the frame, each domain corresponding to an area occupied by at least one selected cell, wherein the one or more domains are located with reference to the detected property of light, and (e) irradiating the non-domain area contained in the frame, wherein each cell present within the non-domain area receives a substantially lethal dose of radiation, whereby one or more cells having a desired product secretion profile are purified. The method can further involve the step of (f) illuminating a further population of the cells, the further population contained in a further frame, and repeating steps (c) through (e).

A method of the invention for purifying one or more selected cells can additionally involve illuminating a yet further population of the cells, the population contained in a yet further frame, and repeating the detecting, locating and irradiating steps. This sequence can be repeated until substantially all of the non-selected cells in the plurality of cells receive a substantially lethal dose of radiation, if desired. In this manner, a single selected cell can be purified. Alternatively, a group of cells can be purified. The purified one or more selected cells can be allowed to proliferate in order to obtain a clonal cell population in the case of one selected cell, or a mixed cell population in the case of more than one selected cell.

In a method of the invention for purifying one or more selected cells, the one or more cells can be selected based on their secretion of a desired product; lack of secretion of an undesired product; level or rate of secretion of the product; or secretion of more than one product. Therefore, in an embodiment, the one or more cells selected when practicing a method of the invention can be identified with reference to a signal value corresponding to an amount of product localized to the capture matrix. The signal value can be determined for an area consistent with the area of the captured secreted product. As such, the area originating the signal value can be determined based on a property of light corresponding to the secreted product. The intensity of the property of light emanating from the area originating the signal value can be assessed using a variety of well known methods, including those described below. Using the integrated area and intensity measurements, a qualitative or quantitative measure of level of secreted product can be generated for each cell. To select a cell that secretes a desired level of product, the signal value corresponding to the amount of product secreted by the cell can be compared to the signal values for the cells of the population in the frame or the plurality of cells being treated.

A signal value corresponding to a level of captured product can be assessed, for example, by (a) identifying the boundary of a cell by detecting a property of light corresponding to the cell to determine the inner boundary of the captured product area, (b) refining the cell boundary, such as by determining a contour 2-4 pixels inner to the cell boundary, and (c) determining the outer boundary of the captured product area based on a property of light corresponding to the captured product or by moving out from the cell boundary by a fixed number of pixels. Following erode algorithms and digital dilation, the area of the captured cellular product can be characterized.

If desired, two or more signal values corresponding to levels of two or more different captured products potentially secreted by a particular cell can be assessed. This application of the method can be used to purify one or more cells that have desired secretion characteristics of two or more products, such as high, intermediate or low level of product secretion as well as no detectable product secretion. For example, one or more cells can be selected to have a high level of secretion of two or more products; a high level of secretion of one product and a low level of secretion of another; a high level of secretion of one product and no detectable secretion of another, and other permutations of levels of secretion. The desired secretion characteristics will depend on the particular use of the cells. For example, a method of the invention can be used to obtain one or more cells that secrete high levels or have similar levels of secretion of two polypeptides that are subunits of an enzyme, or one or more cells that secrete a high level of a cytokine and have no detectable secretion of a protease that degrades the cytokine.

The methods of the invention for purifying one or more selected cells can involve illuminating a population of cells. The cells can be "illuminated" by any source that can provide light energy, including a laser and an arc lamp. It is generally known that many devices could be used in this manner to illuminate the specimen, including, but not limited to, an arc lamp (for example, mercury, xenon, etc.) with or without filters, a light-emitting diode (LED), lasers and the like. A laser for use as an illumination source can be selected, for example, to have high intensity, relatively efficient use of energy, compact size, and minimal heat generation. The light energy can be of any wavelength, such as visible, ultraviolet and infrared light. The light can then be directed by any conventional means, such as mirrors, lenses and beam-splitters, to the population of cells.

Upon illumination, the cells can be observed in a "frame." As used herein, the term "frame," when used in reference to cells illuminated in a method of the invention, means the portion of the plurality of cells that is captured within one frame image captured by the camera. A frame can be contained in a field-of-view, which is the area that is visible through the lens of an apparatus useful for carrying out a method of the invention. A particularly useful frame can have an area of greater than 1 $mm^2$, such as greater than 2 $mm^2$, greater than 4 $mm^2$, greater than 8 $m^2$, greater than 16 $mm^2$, and greater than 32 $mm^2$. A particularly useful field-of-view can have an area of greater than 5 $mm^2$, such as greater than 10 $mm^2$, greater than 20 $mm^2$, greater than 40 $mm^2$, greater than 80 $mm^2$, and greater than 160 $mm^2$.

When the frame is illuminated, one or more properties of light can then be detected from the frame. Non-limiting examples of the detectable properties of light include light having visible, ultraviolet and infrared wavelengths; the intensity of transmittance, reflectance, and fluorescence; linear and circular polarization, and phase-contrast illumination. These properties can be detected by conventional optical devices known to those skilled in the art, including those described in U.S. Pat. No. 6,642,018, which is incorporated herein by reference.

The methods of the invention can involve detecting more than one property of light sequentially or simultaneously. In an embodiment, two distinct detected properties of light correspond to the secreted product and the cells. Therefore, the moieties that generate the detected properties of light can be selected such that simultaneous detection is possible. Those skilled in the art will know how to select appropriate moieties that generate a detectable property of light, for example, based on the emission, absorption and hydrophobic/hydrophilic properties desired, photostability and quantum yield of the moiety. When more than one detectable moiety is used, the selected moiety can have similar or overlapping excitation spectra but different emission spectra, such that the moieties are spectrally distinct. When differentiation between two or more moieties is accomplished by visual inspection, the two or more moieties generally have emission wavelengths of perceptibly different colors to enhance visual discrimination. When differentiation between two or more moieties is accomplished by instrumentation, a variety of filters and diffraction gratings are commercially available to allow the respective emission maxima to be independently detected. When two or more moieties are selected that possess relatively small differences in emission maxima, instrumental discrimination can be enhanced by ensuring that the emission spectra of the two or more moieties have similar integrated amplitudes and similar emission peak widths and that the instrumental system's optical throughput will be equivalent across the emission peak widths of the respective two dyes. Examples of useful combinations of detectable moieties include CELL TRACKER green (used for staining cells) with ALEXA FLUOR 532 or Phycoerythrin (used for detecting secreted product), and CELL TRACKER orange (used for staining cells) with Oregon Green or ALEXA FLUOR 488 (used for detecting secreted product).

The methods of the invention for purifying one or more selected cells involve irradiating non-selected cells with a substantially lethal dose of radiation. The energy beam from the treatment laser is of a wavelength and energy that is useful for achieving immediate or eventual death of the targeted cell. A variety of laser-tissue interactions are known to occur, depending upon the nature of the tissue (for example, light absorbance) and parameters of the laser beam including wavelength and power density, the latter being a function of energy and time of exposure (that is, pulse duration). Photomechanical mechanisms are induced by high power densities ($>10^{10}$ W/cm$^2$) with short laser pulses (<1 ns) (Niemz, M. H., *Laser-tissue interactions: Fundamentals and applications* Berlin: Springer-Verlag (1996)). Photomechanical effects are mediated by breaking of molecular bonds by high-energy photons and formation of ionizing plasma without thermal damage, and are used in medical applications such as corneal and dental surgery. In contrast, photothermal effects are induced when tissue exhibits high light absorption resulting in heat generation. Light absorption by biological tissues is greatest in the infrared (IR) spectrum due to absorption by water. Absorption in the UV and visible spectrum is 5-7 orders of magnitude lower than in IR, such that photothermal effects are difficult to achieve unless mid-IR lasers (for example, Er:YAG at 2940 nm) are used. Such IR lasers are used in medical applications including laser-induced interstitial thermotherapy, but are not well-suited for microscopic applications due to poor transmission by microscope optics and inability to focus to small beam diameters. Photothermal effects can instead be achieved by adding a chromophore to increase absorption at the laser wavelength. In any case, photothermal effects are determined by the temperature achieved in the tissue and the duration of exposure (Niemz, M. H., *Laser-tissue interactions: Fundamentals and applications* Berlin: Springer-Verlag (1996)). Induction of necrosis due to denaturation and coagulation of proteins is first observed at 60° C., and further heating to 80° C. results in cell membrane permeabilization. Finally, photochemical effects, observed mainly in the UV spectrum where biological molecules (that is, proteins, nucleic acids, porphyrins) strongly absorb, result in various forms of tissue damage and can be used to induce apoptosis in targeted cells.

The photothermal mechanism can be implemented by addition of a non-toxic light-absorbing dye (Allura Red). A 10 ns pulsed 523 nm Nd:YLF laser (Spectra-Physics) is focused to a ~5-20 µm diameter spot and then fired at each non-selected cell. Using 4 mg/ml of Allura Red, the $LD_{50}$ was $9\times10^7$ W/cm$^2$, and substantially all target cells were killed at power densities greater than or equal to $2\times10^8$ W/cm$^2$. Photochemical cell elimination can be implemented with a 0.5 ns pulsed laser at 355 nm (JDS Uniphase) focused to a ~5-20 µm diameter spot. The $LD_{50}$ was $2.6\times10^9$ W/cm$^2$, and substantially all target cells were killed at $\geq10^{10}$ W/cm$^2$, principally via induction of apoptosis over a 4-24 hour period. For photomechanical cell elimination, a short-pulsed (0.5 ns) 532 nm laser (JDS Uniphase) was focused down to ~5-20 µm in diameter. The $LD_{50}$ was $2.2\times10^{10}$ W/cm$^2$, and at power densities $\geq8\times10^{10}$ W/cm$^2$, substantially all of the target cells were eliminated resulting in immediate cell lysis.

Particularly useful in the methods of the invention for purifying one or more selected cells are lasers capable of delivering a dose of radiation having an energy density selected from the group of greater than 0.1 J/cm$^2$, greater than 0.3 J/cm$^2$, greater than 1 J/cm$^2$, greater than 3 J/cm$^2$, greater than 10 J/cm$^2$, greater than 30 J/cm$^2$, and greater than 100 J/cm$^2$. Also useful are lasers capable of delivering a dose of radiation having an irradiance selected from the group of greater than $10^7$ W/cm$^2$, greater than $10^8$ W/cm$^2$, greater than $10^9$ W/cm$^2$, greater than $1^{10}$ W/cm$^2$, and greater than $10^{11}$ W/cm$^2$; as used herein, the term irradiance means power per area, and is often expressed in units of watts per square centimeter. Further useful are lasers that deliver radiation having a wavelength selected from the group of between 200 and 400 nm, between 400 and 760 nm, and between 760 and 3000 nm.

The substantially lethal dose of radiation can be delivered to a cell in a variety of modes, including but not limited to a single short pulse of radiation, multiple short pulses of radiation, and a single pulse of radiation having a long duration. The short pulse of radiation can have a duration of less than 1 second, less than 1 millisecond, less than 1 microsecond, less than 1 nanosecond, less than 1 picosecond, and less than 1 femtosecond. Herein, a pulse having duration greater than 1 second is considered to have a long duration.

One skilled in the art would recognize that mechanisms other than those above can be used to eliminate a cell in the methods of the invention. For example, death can be induced in the cells by irradiation that results in release or activation of a toxin in the cell, as commonly used in photodynamic therapy (PDT). In particular, photochemical reactions and uncaging of compounds via the energy beam can be used to control the release of a toxin to eliminate non-selected cells.

Two or more steps of a method of the invention for purifying one or more selected cells can be automated as is described, for example in U.S. Pat. No. 6,642,018, which is incorporated herein by reference.

The methods of the invention for purifying one or more selected cells can involve one or more re-processing steps. For example, if undesired cells remain after irradiation of the non-selected cells, the population of cells can be re-processed.

It is understood that modifications which do not substantially affect the activity of the various embodiments of this invention are also included within the definition of the invention provided herein. Accordingly, the following examples are intended to illustrate but not limit the present invention.

EXAMPLE I

Detection of Individual Cell Product Secretion Based on Detection of Two Properties of Light This example describes the capture and detection of antibody secreted by individual hybridoma cells immobilized in proximity to a capture matrix, with identification of substantially all cells, followed by selection of cells with a desired product secretion profile, ranging from zero (i.e., below the level of detection) to high levels.

UV cross-linking of a 384 well plate (Greiner) was induced by exposure to UV light using the Alpha Imager MultiImage Light Cabinet (Alpha Innotech, San Leandro, Calif.) for 20 minutes on the high (EPI UV) setting. Plates were then rinsed in HBSS (Invitrogen Corporation, Carlsbad, Calif.) to remove debris. Blocking was routinely used between steps, utilizing BSA fraction V (Invitrogen Corporation, Carlsbad, Calif.) for proteins, heat inactivated horse serum (Sigma-Aldrich Co., St. Louis, Mo.) for staining buffers, and heat inactivated FBS (ATCC, Manassas, Va.) for hybridoma cell treatments. Protein G was added to each well (1.0 to 10 μg) in PBS with 0.1% BSA (Invitrogen Corporation, Carlsbad, Calif.). Wells were allowed to dry, and were then washed with RPMI (Invitrogen Corporation, Carlsbad, Calif.). Ability of the capture matrix, which contained protein G, to localize IgG antibody was verified by measuring fluorescence after adding PE-conjugated goat-anti-mouse IgG (Molecular Probes, Eugene, Oreg.) and performing repetitive washings and competitions with non-labeled anti-mouse controls (Molecular Probes, Eugene, Oreg.). Hybridoma cells (172-12A4; ATCC, Manassas, Va.), producing an anti-v-erbB IgG, were added at 200 cells per well in RPMI with 10% FBS. Plates were incubated at 37° C. for 48 hours to allow IgG production and secretion. The capture matrix immobilized the cells, keeping each cell in proximity to its secreted products during the incubation and subsequent steps. To detect the produced antibody, an agent, comprising an 11 amino acid peptide corresponding to residues 138 to 149 of the human EGF receptor (IMVKCWMIDAD) was biotinylated (Invitrogen Corporation, Carlsbad, Calif.) and added to wells at 3 nanomoles per well for an overnight incubation at 37° C. allowing for selective binding to the produced IgG. The agent further comprised streptavidin-AlexaFluor-532 (Molecular Probes, Eugene, Oreg.), which was added at 1 μg per well. cells were also contacted with a reagent comprising Syto13 (Molecular Probes, Eugene, Oreg.) that bound to substantially all of the cells. After incubation for at least an hour at room temperature, wells were washed with HBSS with 2.5% horse serum until background was insignificant (about 8 to 10 times). A population of cells was then illuminated with 485 nm and 532 nm light for excitation of Styo13 and AlexaFluor-532, respectively. Fluorescence was detected in a CCD camera behind 530 nm and 645 nm filters for Syto13 and AlexaFluor-532, respectively.

A pseudo-color representation of the resulting two-color fluorescence is shown in FIG. 1. Substantially all cells were located with reference to green Syto13 fluorescence, and secreted product was identified with reference to red AlexaFluor-532 fluorescence. Note that the pseudo-color image displays red and green overlap as yellow. Manual selection of cells with the desired secretion profile was easily performed using such images. Alternatively, automated image processing was used to determine a quantitative signal value for each cell based on the integrated red intensity in the annular region extending from the cell membrane to approximately 10 μm out. Four representative cells are circled and numbered in panel A, and shown magnified in the panels labeled 1 to 4. Panels 1 to 4 show the annular region within which the integrated red intensity was calculated. The signal value was 2907 for cell 1 (high secretor), 1440 for cell 2 (moderate secretor), 141 for cell 3 (low secretor), and 1.1 for cell 4 (undetectable above background; essentially zero secretion). This manual or automated locating of all cells and selected is used to locate and irradiate non-selected cells, resulting in purification of one or more selected cells.

EXAMPLE II

Detection of Individual Cell Product Secretion Based on Detection of One Property of Light This example describes the capture and detection of antibody secreted by individual hybridoma cells immobilized in proximity to a capture matrix, followed by selection of cells with low to high levels of product secretion and locating of domain areas occupied by-the selected cells.

A capture matrix within 384 well plates was prepared as described in Example I. Hybridoma cells (172-12A4; ATCC, Manassas, Va.), producing an anti-v-erbB IgG, were added at 200 cells per well in RPMI with 10% FBS. Plates were incubated at 37° C. for 48 hours to allow IgG production and secretion. The agent, as described in Example I, was added to the wells to selectively bind to the produced IgG. After washing, a population of cells was illuminated with 532 nm light for excitation of AlexaFluor-532. Fluorescence was detected in a CCD camera behind a 645 nm filter.

Figure 2:
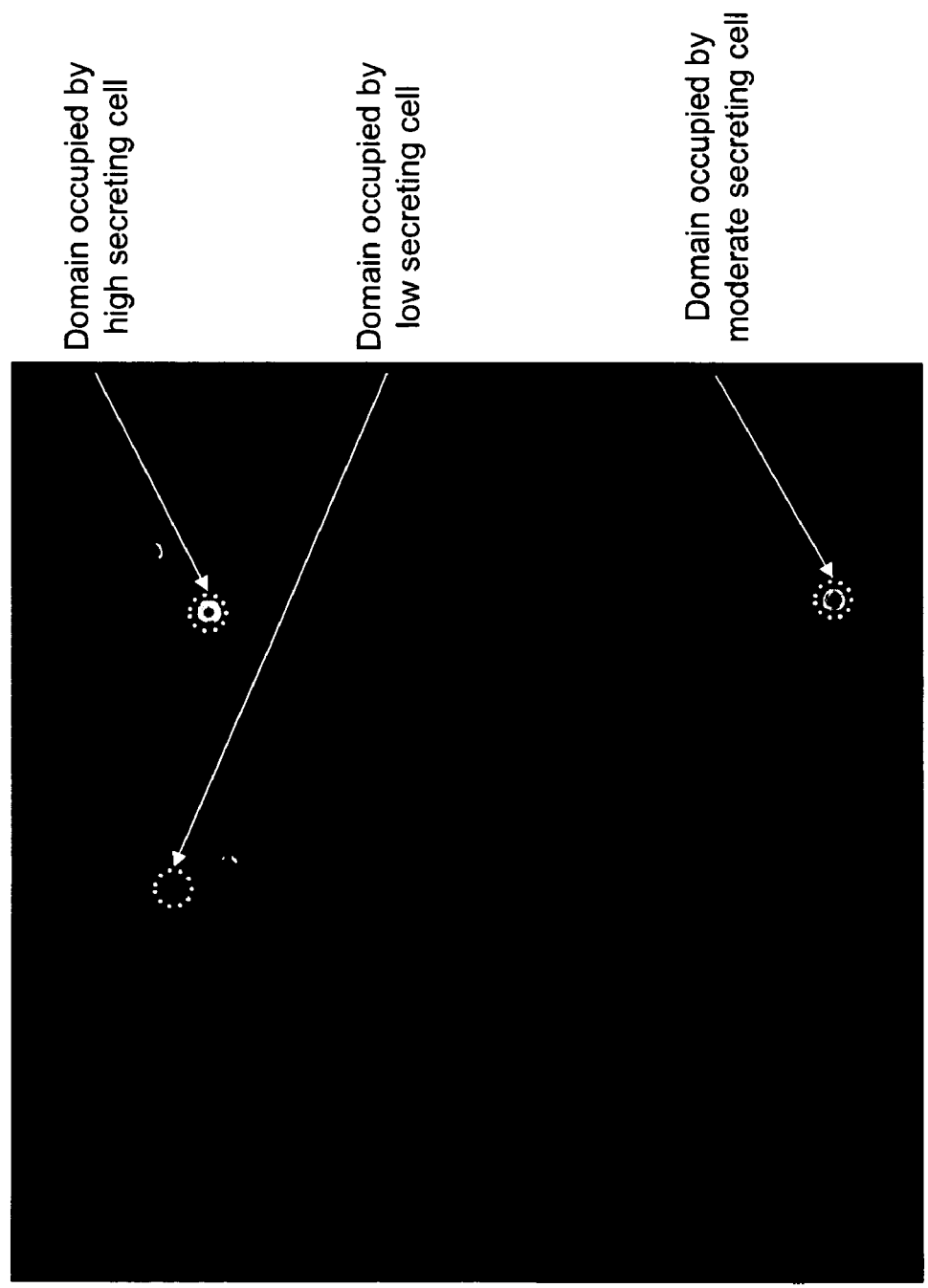
FIG. 2 shows in situ localization and detection of secreted antibody, and the locating of domains corresponding to areas occupied by selected cells.

A representation of the resulting fluorescence image is shown in FIG. 2. Selected cells were identified with reference to the detected fluorescence, and domains corresponding to areas occupied by one or more selected cells were then located. The non-domain area was then irradiated using a grid pattern of laser shots such that each non-selected cell within the non-domain area received a lethal dose. With a 20 μm laser beam diameter, a grid with 20 μm spacing between center points results in lethal irradiation of each non-selected cell, regardless of its position in the non-domain area. The selected cells in the domain areas are not irradiated and thus are spared, resulting in purification of the selected cells.

EXAMPLE III

Purification of Cells Based on Product Secretion

This example describes generation of three clonal hybridoma cell lines.

To select hybridoma cells, the capture matrix, cells, product-binding agent, and methods were as described in Example I, except that the cell-binding agent used was CellTracker™ Orange (Molecular Probes, Eugene, Oreg.). Prior to illumination, Media 199 (Invitrogen Corporation, Carlsbad, Calif.) containing 4 mg/ml FD&C Red 40 (Warner-Jenkinson Company, St. Louis, Mo.) was added in preparation for photo-thermal laser-mediated cell purification. All cells were located by CellTracker Orange fluorescence, and selected cells were located by AlexaFluor 532 fluorescence in the area around each cell, as shown in FIG. 1. The single cell with the highest level of IgG production was selected within each well, and each non-selected cell was irradiated with 10 J/cm$^2$ delivered from a 10 ns pulsed 523 nm semi-conductor laser (Spectra-Physics) using the apparatus described in U.S. Pat. No. 6,534,308.

Figure 3:
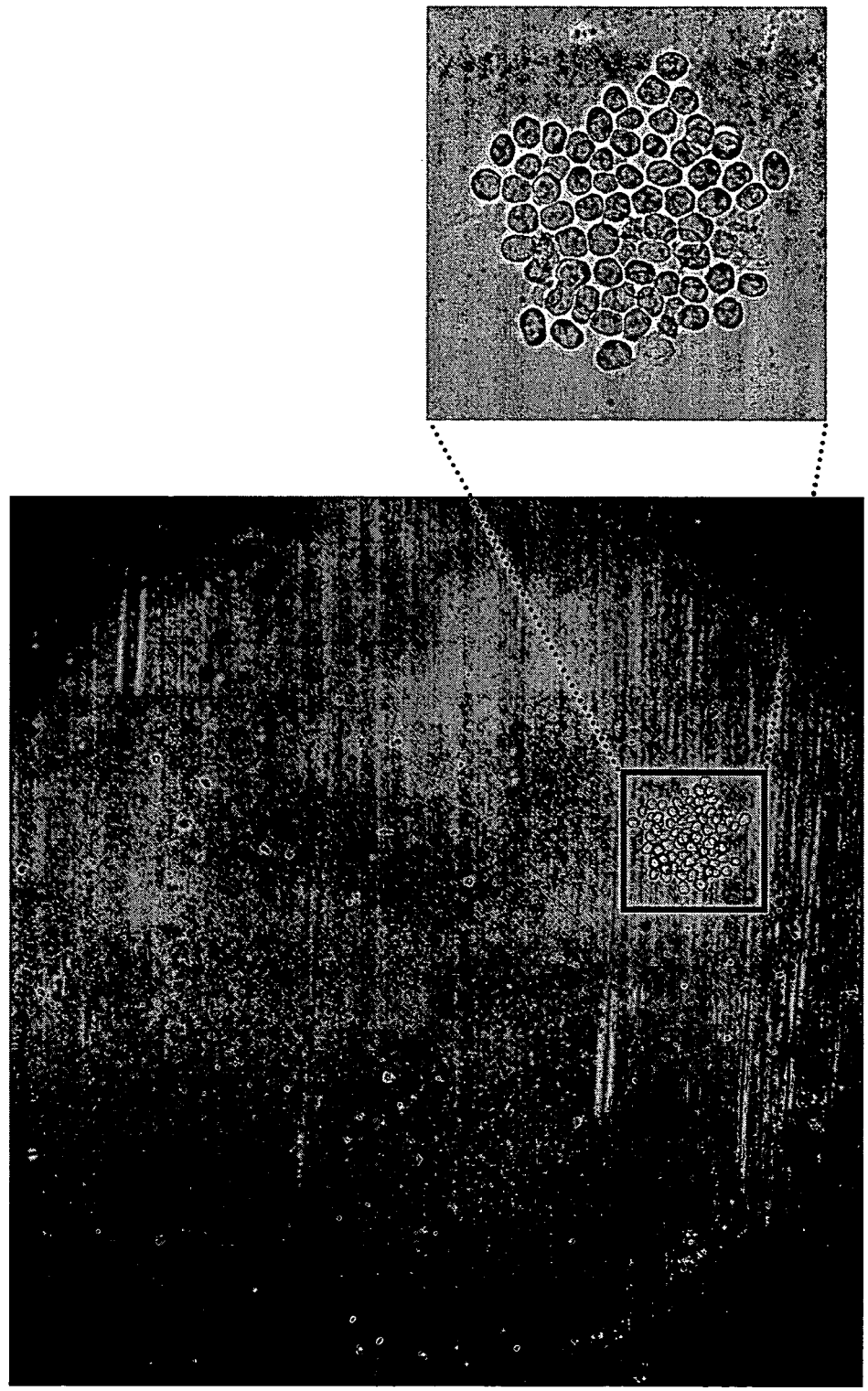
FIG. 3 shows proliferation of a selected and purified cell.

Medium was then added, and plates were incubated to allow the purified selected cell to proliferate within each well. After 48 hours, wells were examined with a microscope. The signal from the product-binding agent still remained visible and grew in size around the selected cell, verifying that it was viable and the only remaining cell in the well. In cases were more than one cell remained in the well, the irradiating step was repeated. As single clonal populations became evident in each well (FIG. 3), they were transferred to standard 96 well plates for further proliferation. After proliferation of each clone to about 2,500 cells, they were transferred to 24 well plates in 2 ml of medium.

Figure 4:
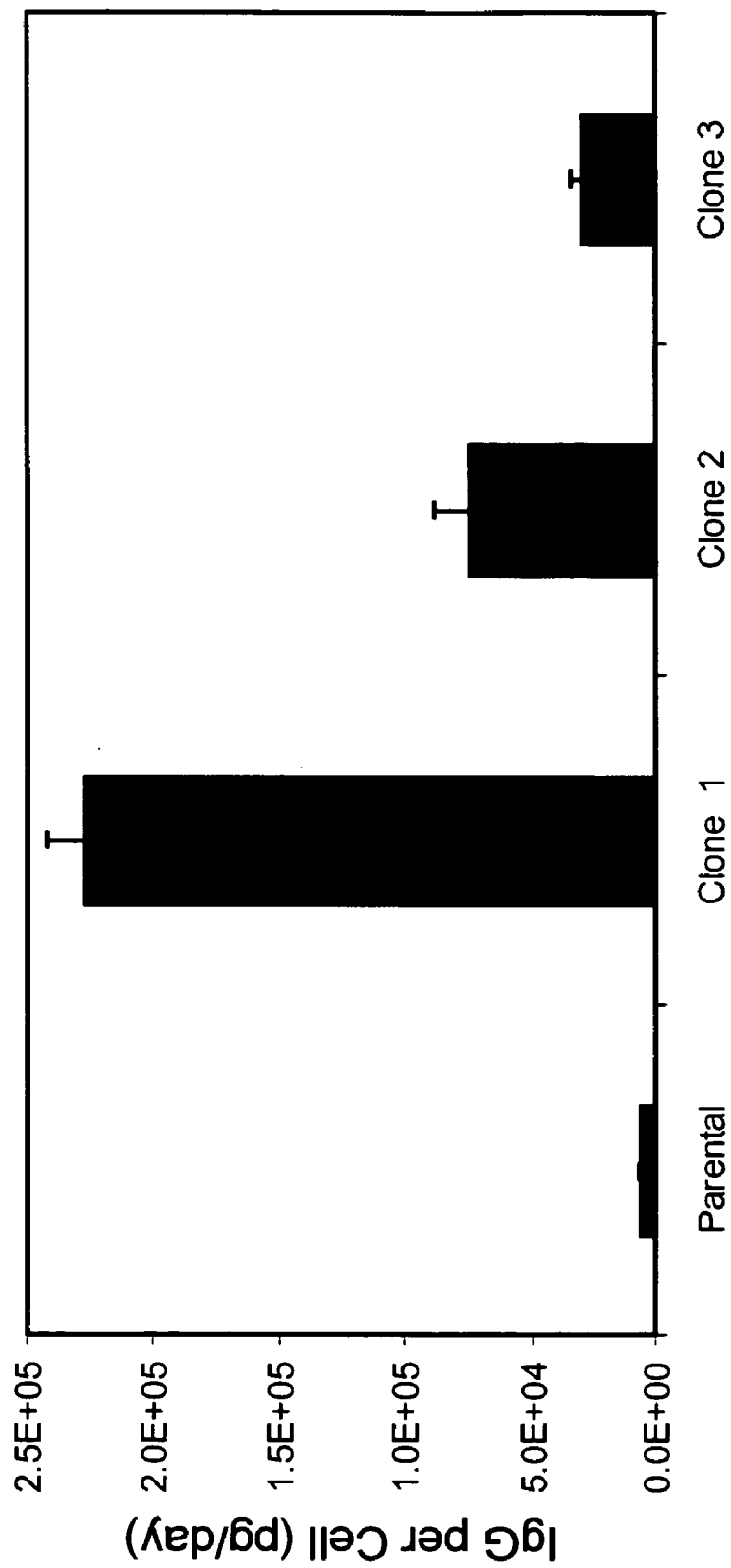
FIG. 4 shows antibody secretion rates (pg/day) from a parental hybridoma cell line (Parental) and three clonal populations that were obtained from cells purified based on product secretion (Clone 1, Clone 2 and Clone 3).

Every 48 hours, 1 ml of medium was transferred to a tube and flash frozen. Fresh medium was added to each well. This process was repeated for 5 cycles (that is, 10 days). At the end of the process, the aliquots were thawed, combined, and 1 ml was purified using a Protein-A column (Hi-Trap; Amersham, Piscataway, N.J.). The purified protein was then run through PD-10 de-salting columns. The final product was characterized by ELISA. The amount of antibody produced by selected clones is shown in FIG. 4. Note the significantly improved level of antibody secretion in each selected clonal line as compared to the parental cell line.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A method for purifying one or more selected cells in a population, comprising:
   (a) contacting a plurality of cells immobilized in proximity to a capture matrix that localizes a product secreted by one or more of the cells with an agent that selectively binds to the product, wherein the agent generates a signal detectable as a property of light;
   (b) illuminating a population of the cells, contained in a frame;
   (c) detecting two or more properties bf light directed from the frame, wherein a first property of light identifies substantially all cells of the population, and a second property of light identifies product localized to the capture matrix;
   (d) locating substantially all cells of the population with reference to the detected first property of light;
   (e) selecting one or more cells with reference to the detected second property of light; and
   (f) irradiating the one or more non-selected cells, wherein each the one or more non-selected cells receives a substantially lethal dose of radiation,
   whereby one or more selected cells having a desired product secretion profile are purified.

2. The method of claim 1, wherein the product is selected from the group consisting of a polypeptide, an antibody, an antibody fragment, a cytokine, a growth factor, an enzyme, a hormone, a neurotransmitter, a signaling molecule, and a therapeutic protein.

3. The method of claim 1, wherein the capture matrix comprises a substance selected from the group consisting of Protein G, Protein A, an antibody, an antibody fragment, an aptamer, and a ligand for the product.

4. The method of claim 1, wherein the capture matrix comprises a gel.

5. The method of claim 1, further comprising the step of (g) illuminating a further population of the cells, the further population contained in a further frame, and repeating steps (c) through (f).

6. The method of claim 1, wherein the one or more selected cells are cells that produce a high level of product relative to other cells of the population.

7. The method of claim 1, wherein the one or more selected cells are cells that produce a low level of product relative to other cells of the population.

8. The method of claim 1, wherein the one or more selected cells are cells that produce an undetectable level of product.

9. The method of claim 5, further comprising repeating step (g) followed by steps (c) through (f) until substantially all of the non-selected cells in the plurality of cells receive a substantially lethal dose of radiation.

10. The method of claim 9, wherein the one or more selected cells are cells that produce a high level of product relative to other cells of the plurality.

11. The method of claim 9, wherein the one or more selected cells are cells that produce a low level of product relative to other cells of the plurality.

12. The method of claim 9, wherein the one or more selected cells are cells that produce an undetectable level of product.

13. The method of claim 1, further comprising allowing the purified one or more selected cells to proliferate.

14. The method of claim 1, wherein steps (b) through (f) are automated.

15. The method of any of claims 1, 5 or 9, wherein the frame is a portion of a field-of-view, the field-of view having an area greater than 80 mm$^2$.

16. The method of claim 1, Wherein the agent that selectively binds to the product is selected from the group consisting of an antibody, an antibody fragment, an aptamer, a substrate, and a ligand.

17. The method of claim 1, wherein the one or more selected cells are identified with reference to a signal value corresponding to an amount of product localized to the capture matrix in the vicinity of thc one or more selected cells.

18. The method of claim 1, wherein the substantially lethal dose of radiation is delivered to each non-selected cell in one or more radiation pulses.

19. The method of claim 1, wherein the substantially lethal dose of radiation has an energy density selected from the group consisting of greater than 0.1 J/cm$^2$, greater than 0.3 J/cm$^2$, greater than 1 J/cm$^2$, greater than 3 J/cm$^2$, greater than 10 J/cm$^2$, greater than 30 J/cm$^2$, and greater than 100 J/cm$^2$.

20. The method of claim 1, wherein the substantially lethal dose of radiation has an irradiance selected from the group consisting of greater than 10$^7$ W /cm$^2$, greater than 10$^8$ W/cm$^2$, greater than 10$^9$ W/cm$^2$, greater than 10$^{10}$ W/cm$^2$, and greater than 10$^{11}$ W/cm$^2$.

21. The method of claim 1, wherein the radiation comprises an electromagnetic radiation having a wavelength selected from the group consisting of between 200 and 400 nm, between 400 and 760 nm, and between 760 and 3000 nm.

22. The method of claim 1, wherein prior to illumination, the plurality of cells is contacted with a reagent that selectively binds to substantially all of the cells, the reagent generates a signal detectable as a first property of light.

23. A method for purifying one or more selected cells in a population, comprising:
   (a) illuminating a population of cells in a frame, wherein the illuminated cells are contained in a plurality of cells immobilized in proximity to a capture matrix, wherein the capture matrix localizes a product secreted by one or more of the cells;
   (b) detecting two or more properties of light directed from the frame, wherein a first property of light identifies substantially all cells of the population, and wherein a second properly of light identifies product localized to the capture matrix;

(c) locating substantially all cells of the population with reference to the detected first property of light;

(d) selecting one or more cells with reference to the detected second property of light; and (e) irradiating the one or more non-selected cells, wherein each of one or more non-selected cells receives a substantially lethal dose of radiation, whereby one or more selected cells having a desired product secretion profile arc purified.

24. The method of claim 23, wherein the product is selected from tbe group consisting of a polypeptide, an antibody, an antibody fragment, a cytokine, a growth factor, an enzyme, a hormone, a neurotransmitter, a signaling molecule, arid a therapeutic protein.

25. The method of claim 23; wherein the capture matrix comprises a substance selected from the aroup consisting of Protein G, Protein A, an antibody, an antibody fragment, an aptamer, and a ligand for the product.

26. The method of claim 23, wherein the capture matrix comprises a gel.

27. The method of claim 23, further comprising the step of (f) illuminating a further population of the cells, the further population contained in a further frame, and repeating steps (b) through (e).

28. The method of claim 23, wherein the one or more selected cells are cells that produce a high level of product relative to other cells of the population.

29. The method of claim 23, wherein the one or more selected cells are cells that produce a low level of product relative to other cells of the population.

30. The method of claim 23, wherein the one or more selected cells are cells that produce an undetectable level of product.

31. The method of claim 27, further comprising repeating step (f) followed by steps (b) through (e) until substantially all of the non-selected cells in the plurality of cells receive a substantially lethal dose of radiation.

32. The method of claim 31, wherein the one or more selected cells are cells that produce a high level of product relative to other cells of the plurality.

33. The method of claim 31, wherein the one or more selected cells are cells that produce a low level of product relative to other cells of the plurality.

34. The method of claim 31, wherein the one or more selected cells are cells that produce an undetectable level of product.

35. The method of claim 23, further comprising allowing the purified one or more selected cells to proliferate.

36. The method of claim 23, wherein steps (a) through (e) are automated.

37. Thc method of any of claims 23, 27 or 31, wherein the frame is a portion of a field-of-view, the field-of-view having an area greater than 80 mm$^2$.

38. The method of claim 23, wherein the one or more selected cells are identified with reference to a signal value corresponding to an amount of product localized to the capture matrix in the vicinity of the one or more selected cells.

39. The method of claim 23, wherein the substantially lethal dose of radiation is delivered to each non-selected cell in one or more radiation pulses.

40. The method of claim 23, wherein the substantially lethal dose of radiation has an energy density selected from the group consisting of greater than 0.1 J/cm$^2$, greater than 0.3 J/cm$^2$, greater than 1 J/cm$^2$, greater than 3 J/cm$^2$, greater than 10 J/cm$^2$, greater than 30 J/cm$^2$, and greater than 100 J/cm$^2$.

41. The method of claim 23, wherein the substantially lethal dose of radiation has an irradiance selected from the group consistin2 of greater than 10$^7$ W/cm$^2$, greater than 10$^8$ W/cm$^2$, greater than 10$^9$ W/cm$^2$, greater than 10$^{10}$ W/cm$^2$, and greater than 10$^{11}$ W/cm$^2$.

42. The method of claim 23, wherein the radiation comprises an electromagnetic radiation having a wavelength selected from the group consisting of between 200 and 400 nm, between 400 and 760 nm, and between 760 and 3000 nm.

43. The method of claim 23, wherein prior to illuminating, the plurality of cells is contacted with a reagent that binds to substantially all of the cells, the reagent generates a signal detectable as a first property of light.

44. A method for purifying one or more selected cells in a population cells, comprising:

(a) illuminating a population of cells in a frame, wherein the illuminated cells are contained in a plurality of cells immobilized in proximity to a capture matrix, wherein the capture matrix localizes a product secreted by one or more of the cells;

(b) detecting at least one property of light directed from the frame, wherein the at least one property of light identifies product localized to the capture matrix;

(c) locating and selecting (i) one or more cells with reference to the detected property of light, and (ii) one or more domains in the frame, each domain corresponding to an area occupied by the one or more selected cells, wherein the one or more domains are located with reference to the detected property of light;

(d) irradiating the non-domain area. contained in the frame, wherein substantially all cells present within the non-domain area receive a substantially lethal dose of radiation, whereby the one or more selected cells having a desired product secretion profile are purified.

45. The method of claim 44, wherein the product is selected from the aroun consisting of a polypeptide, an antibody, an antibody fragment, a cytokine, a growth factor, an enzyme, a hormone, a neurotransmitter, a signaling molecule, and a therapeutic protein.

46. The method of claim 44, wherein the capture matrix comprises a substance selected from the group consisting of Protein G, Protein A, an antibody, an antibody fragment, an aptamer, and a ligand for the product.

47. The method of claim 44, wherein the capture matrix comprises a gel.

48. The method of claim 44, further comprising the step of (e) illuminating a further population of the cells, the further population contained in a further frame, and repeating steps (b) through (d).

49. The method of claim 44 or wherein the one or more selected cells comprise a product secretion profile characterized by producing a high level of product relative to other cells of the population.

50. The method of claim 44, wherein the one or more selected cells comprise a product secretion profile characterized by producing a low level of product relative to other cells of the population.

51. The method of claim 44, wherein the one or more selected cells are cells that produce an undetectable level of product relative to other cells of the population.

52. The method of claim 48, further comprising repeating step (e) followed by steps (b) through (d) until substantially all of the non-selected cells in the plurality of cells receive a substantiafly lethal dose of radiation.

53. The method of claim 52, wherein the one or more selected cells are cells that produce a high level of product relative to other cells of the plurality.

54. The method of claim 52, wherein the one or more selected cells are cells that produce a low level of product relative to other cells of the plurality.

55. The method of claim 52, wherein the one or more selected cells are cells that produce an undetectable level of product relative to other cells of the plurality.

56. The method of claim 44, further comprising allowing the purified one or more selected cells to proliferate.

57. The method of claim 44, wherein steps (a) through (d) are automated.

58. The method of any of claims 44, 48 or 52, wherein the frame is a portion of a field-of-view, the field-of-view having an area greater than 80 mm$^2$.

59. The method of claim 44, wherein the one or more selected cells are identified with reference to a signal value corresponding to an amount of product localized to the capture matrix in the vicinity of the one or more selected cells.

60. The method of claim 44, wherein the substantially lethal dose of radiation is delivered in one or more radiation pulses to each cell present within the non-domain area.

61. The method of claim 44, wherein the substantially lethal dose of radiation has an energy density selected from the group consisting of greater than 0.1 J/cm$^2$, greater than 0.3 J/cm$^2$, greater than 1 J/cm$^2$, greater than 3 J/cm$^2$, greater than 10 J/cm$^2$, greater than 30 J/cm$^2$, and greater than 100 J/cm$^2$.

62. The method of claim 44, wherein the substantially lethal dose of radiation has an irradiance selected from the, group consisting of greater than 10$^7$ W/cm$^2$, greater than 10$^8$ W/cm$^2$, greater than 10$^9$ W/cm$^2$, greater than 10$^{10}$ W/cm$^2$, and greater than 10$^{11}$ W/cm$^2$.

63. The method of claim 44, wherein the radiation comprises an electromagnetic radiation having a wavelength selected from the group consisting of between 200 and 400 nm, between 400 and 760 nm, and between 760 and 3000 nm.

64. A method for purifying one or more selected cells in a population of cells, comprising:
   (a) contacting a plurality of cells immobilized in proximity to a capture matrix, wherein the capture matrix localizes a product secreted by one or more of the plurality of cells, with an agent that selectively binds to the product, wherein the agent generates a signal detectable as a property of light;
   (b) illuminating a population of the pluraliw of cells, the population contained in a frame;
   (c) detecting at least one property of light directed from the frame, wherein a property of light identifies product localized to the capture matrix;
   (d) locating and selecting one or more cells with reference to the detected property of light
   (e) selecting one or more domains in the frame, each domain corresponding to an area occupied by at least one selected cell, wherein the onc or more domains are located with reference to the detected property of light, and
   (f) irradiating one or more non-domain areas contained in. the frame, wherein each cell present within the non-domain areas receives a substantially lethal dose of radiation,
   whereby one or more selected cells having a desired product secretion profile are purified.

65. The method of claim 64, wherein the product is selected from the group consisting of a polypeptide, an antibody, an antibody fragment, a cytokine, a growth factor, an enzyme, a hormone, a neurotransmitter, a signaling molecule, and a therapeutic protein.

66. The method of claim 64, wherein the capture matrix comprises a substance selected from the group consisting of Protein G, Protein A, an antibody, an antibody fragment, an aptamer, and a ligand for the product.

67. The method of claim 64, wherein the capture matrix comprises a gel.

68. The method of claim 64, further comprising the step of (g) illuminating a further population of the cells, the further population contained in a further frame, and repeating steps (c) through (f).

69. The method of claim 64, wherein the one or more selected cells are cells that produce a high level of product relative to other cells of the population.

70. The method of claim 64, wherein the one or more selected cells are cells that produce a low level of product relative to other cells of the population.

71. The method of claim 64, wherein the one or more selected cells are cells that produce an undetectable level of product relative to other cells of the population.

72. The method of claim 68, further comprising repeating step (g) followed by steps (c) through (f) until substantially all of the non-selected cells in the plurality of cells rcccive a substantially lethal dose of radiation.

73. The method of claim 72, wherein the one or more selected cells are cells that produce a high level of product relative to other cells of the plurality.

74. The method of claim 72, wherein the one or more selected product-secreting cells are cells that produce a low level of product relative to other cells of the plurality.

75. The method of claim 72, wherein the one or more selected cells are cells that produce an undetectable level of product relative to other cells of the plurality.

76. The method of claim 64, further comprising allowing the purified one or more selected cells to proliferate.

77. The method of claim 64, wherein steps (b) through (f) are automated.

78. The method of any of claims 64, 68 or 72, wherein the frame is a portion of a field-of-view, the field-of-view having an area greater than 80 mm$^2$.

79. The method of claim 64, wherein the agent that selectively binds to the product is selected from the group consisting of an antibody, an antibody fragment, an aptamer, a substrate, and a ligand.

80. The method of claim 64, wherein the one or more selected cells are identified with reference to a signal value corresponding to an amount of product localized to the capture matrix in the vicinity of the one or more selected cells.

81. The method of claim 64, wherein the substantially lethal dose of radiation is delivered in one or more radiation pulses to each cell present within the non-domain area.

82. The method of claim 64, wherein the substantially lethal dose of radiation has an energy density selected from the group consisting of greater than 0.1 J/cm$^2$, greater than 0.3 J/cm$^2$, greater than 1 J/cm$^2$, greater than 3 J/cm$^2$, greater than 10 J/cm$^2$, greater than 30 J/cm$^2$, and greater than 100 J/cm$^2$.

83. The method of claim 64, wherein the substantially lethal dose of radiation has an irradiance selected from the group consisting of greater than 10$^7$ W/cm$^2$, greater than 10$^8$ W/cm$^2$ greater than 10$^9$ W/cm$^2$ greater than 10$^{10}$ W/cm$^2$, and greater than 10$^{11}$ W/cm$^2$.

84. The method of claim 64, wherein the radiation comprises an electromagnetic radiation having a wavelength selected from the group of between 200 and 400 nm, between 400 and 760 nm, and between 760 and 3000 nm.

85. A method for determining the product secretion profile of one or more cellsj oulation of cells, comprising:
   (a) illuminating a population of cells in a frame, wherein the illuminated cells are contained in a plurality of cells immobilized in proximity to a capture matrix, wherein the capture matrix localizes a product secreted by one or more of the cells;

(b) detecting at least one property of light directed from the frame, wherein a property of light identifies product localized to the capture matrix;

(c) locating one or more cells with reference to the detected property of light, and;

(d) determining a quantitative signal value from the property of light indicative of the product secretion profile of the one or more cells.

86. A method for determining the product secretion profile of one or more cells in a population of cells comprising:

(a) contacting a plurality of cells immobilized in proximity to a capture matrix, wherein the capture matrix localizes a product secreted by one or more of the cells, with an agent that selectively binds to the product, wherein the agent generates a signal detectable as a property of light;

(b) illuminating a population of the cells, the population contained in a frame, wherein the illuminated population is contained within the plurality of cells;

(c) detecting at least one property of light directed from the frame, wherein a property of light identifies product localized to the capture matrix;

(d) locating one or more cells with reference to the detected property of light, and;

(e) determining a quantitative signal value from the property of light indicative of a product secretion profile.

87. The method of claim 85 or 86, wherein the product is an antibody.

88. The method of claim 87, wherein the quantitative signal value is used to select cells for purification.

89. The method of claim 88, wherein the selected cells produce high-levels of recombinant humanized antibody relative to other cells in the population.

90. A method for purifying one or more selected cells in a population of cells, comprising:

providing a population of cells immobilized in proximity to a capture matrix, wherein the capture matrix localizes a product secreted by one or more of the cells;

contacting the population of cells with an agent that selectively binds to the product, wherein the agent generates a signal detectable as a property of light;

illuminating the population of the cells;

detecting two or more properties of light, wherein a first property of light identifies substantially all of the population of cells, and a second property of light identifies a product localized to the capture matrix;

locating substantiaUy all of the population of cells with reference to the detected first property of light;

selecting one or more cells from the population of cells with reference to the detected second property of light; and irradiafmg a non-selected cell, wherein the non-selected cell receives a substantially lethal dose of radiation, whereby the one or more selected cells having a desired product secretion profile are purified.

\* \* \* \* \*

UNITED STATES PATENT AND TRADEMARK OFFICE
CERTIFICATE OF CORRECTION

PATENT NO. : 7,425,426 B2
APPLICATION NO. : 10/801931
DATED : September 16, 2008
INVENTOR(S) : Koller et al.

It is certified that error appears in the above-identified patent and that said Letters Patent is hereby corrected as shown below:

At page 2 column 2, line 18, please delete "Marow" and insert therefore, --Marrow--.

At page 2 column 2, line 26, please delete "377." and insert therefore, --377--.

At page 2 column 2, line 33, please delete "Immunologic" and insert therefore, --immunologic--.

At page 3 column 2, line 5, please delete "rsik" and insert therefore, --risk--.

At page 3 column 2, line 18, please delete "189" and insert therefore, --184--.

At column 10, line 60, please delete "-of" and insert therefore, --of--.

At column 12, line 37, please delete "8 $m^2$," and insert therefore, --8 $mm^2$,--.

At column 13, line 20, please delete "ceils" and insert therefore, --cells--.

At column 14, line 20, please delete "$1^{10}$" and insert therefore, --$10^{10}$--.

At column 17, line 33, please delete "cells," and insert therefore, --cells--.

At column 17, line 35, please delete "bf" and insert therefore, --of--.

At column 17, line 45, before "the" please delete "each".

At column 17, line 45, please delete "receives" and insert therefore, --receive--.

At column 18, line 24, please delete "of view" and insert therefore, --of-view--.

At column 18, line 26, please delete "Wherein" and insert therefore, --wherein--.

At column 18, line 33, please delete "thc" and insert therefore, --the--.

At column 18, line 66, please delete "properly" and insert therefore, --property--.

At column 19, line 5, before "one" please delete "the".

At column 19, line 6, after "of" please add --the--.

UNITED STATES PATENT AND TRADEMARK OFFICE
CERTIFICATE OF CORRECTION

PATENT NO.        : 7,425,426 B2
APPLICATION NO.   : 10/801931
DATED             : September 16, 2008
INVENTOR(S)       : Koller et al.

It is certified that error appears in the above-identified patent and that said Letters Patent is hereby corrected as shown below:

At column 19, line 9, please delete "arc" and insert therefore, --are--.

At column 19, line 11, please delete "tbe" and insert therefore, --the--.

At column 19, line 13, please delete "arid" and insert therefore, --and--.

At column 19, line 15, please delete "claim 23;" and insert therefore, --claim 23,--.

At column 19, line 16, please delete "aroup" and insert therefore, --group--.

At column 19, line 51, please delete "Thc" and insert therefore, --The--.

At column 20, line 1, please delete "consistin2" and insert therefore, --consisting--.

At column 20, line 13, after "population" please add --of--.

At column 20, line 29, please delete "area." and insert therefore, --area--.

At column 20, line 35, please delete "aroun" and insert therefore, --group--.

At column 20, line 49, please delete "claim 44 or" and insert therefore, --claim 44,--.

At column 20, line 64, please delete "substantiafly" and insert therefore, --substantially--.

At column 21, line 27, please delete "the," and insert therefore, --the--.

At column 21, line 43, please delete "pluraliw" and insert therefore, --plurality--.

At column 21, line 52, please delete "onc" and insert therefore, --one--.

At column 21, line 55, please delete "in." and insert therefore, --in--.

At column 22, line 20, please delete "rcccive" and insert therefore, --receive--.

At column 22, line 58, please delete "W/cm$^2$ greater than 10$^9$ W/cm$^2$ greater" and insert therefore, --W/cm$^2$, greater than 10$^9$ W/cm$^2$, greater--.

UNITED STATES PATENT AND TRADEMARK OFFICE
CERTIFICATE OF CORRECTION

PATENT NO. : 7,425,426 B2
APPLICATION NO. : 10/801931
DATED : September 16, 2008
INVENTOR(S) : Koller et al.

It is certified that error appears in the above-identified patent and that said Letters Patent is hereby corrected as shown below:

At column 22, line 65, please delete "cellsj oulation" and insert therefore, --cells in a population--.

At column 23, line 1, please delete "wberein" and insert therefore, --wherein--.

At column 23, line 12, please delete "detennining" and insert therefore, --determining--.

At column 23, line 13, after "of cells" please add --,--.

At column 23, line 24, please delete "thc" and insert therefore, --the--.

At column 24, line 20, please delete "substantiaUy" and insert therefore, --substantially--.

At column 24, line 25, please delete "irradiafmg" and insert therefore, --irradiating--.

Signed and Sealed this

Thirtieth Day of June, 2009

JOHN DOLL
*Acting Director of the United States Patent and Trademark Office*